United States Patent
Brown et al.

[11] Patent Number: 5,917,034
[45] Date of Patent: Jun. 29, 1999

[54] ANTITHROMBOTIC N-AMIDINOPIPERIDINE AND BENZAMIDINE DERIVATIVES

[75] Inventors: Alan Daniel Brown; John Christopher Danilewicz; Paul Vincent Fish, all of Sandwich, United Kingdom

[73] Assignee: Pfizer Inc., New York, N.Y.

[21] Appl. No.: 09/029,260

[22] PCT Filed: Oct. 21, 1996

[86] PCT No.: PCT/EP96/04610

§ 371 Date: Mar. 9, 1998

§ 102(e) Date: Mar. 9, 1998

[87] PCT Pub. No.: WO97/16444

PCT Pub. Date: May 9, 1997

[30] Foreign Application Priority Data

Nov. 2, 1995 [GB] United Kingdom ............ 9522495

[51] Int. Cl.$^6$ .............. C07D 401/12; C07D 401/14; C07D 405/14; C07D 409/14
[52] U.S. Cl. .................. 540/597; 540/607; 546/187; 546/189; 546/194; 546/226
[58] Field of Search .................. 546/189, 226, 546/187, 194; 540/597, 607

[56] References Cited

U.S. PATENT DOCUMENTS

| | | | |
|---|---|---|---|
| 5,346,907 | 9/1994 | Kerwin, Jr. et al. | 514/312 |
| 5,561,146 | 10/1996 | Kim et al. | 514/326 |

FOREIGN PATENT DOCUMENTS

| | | |
|---|---|---|
| 0623595 | 11/1994 | European Pat. Off. . |
| 0648780 | 4/1995 | European Pat. Off. . |
| 0686642 | 12/1995 | European Pat. Off. . |
| WO9513274 | 5/1995 | WIPO . |

OTHER PUBLICATIONS

Alig et al, Chemical Abstract vol. 118, No. 125071, "N–Acyl–Alpha Amino Acids Method for Their Preparation and Then Use for the Treatment of Diseases" 1992.

Primary Examiner—John Kight
Assistant Examiner—Raymond Covington
Attorney, Agent, or Firm—Peter C. Richardson; Gregg C. Benson; A. Dean Olson

[57] ABSTRACT

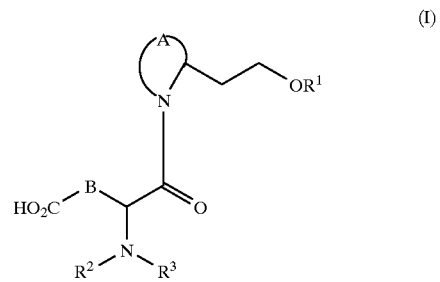

(I)

Compounds of formula (I), pharmaceutically acceptable salts thereof, and pharmaceutically acceptable solvates of either entity, wherein A is optionally monosaturated $C_1$–$C_4$ alkylene optionaly monounsaturatred with $C_1$–$C_4$ alkyl; B is $C_1$–$C_3$ alkylene optionally substituted with $C_1$–$C_4$ alkyl; $R^1$ is N-amidino-4-piperidyl or 4-amidinophenyl; $R^2$ is $C_4$–$C_{12}$ alkyl; ($C_3$–$C_8$ cycalkyl)$C_1$–$C_4$ alkylene; optionally methylene-bridged $C_5$–$C_8$ cycloalkyl optionally substituted with one to three $C_1$–$C_4$ alkyl groups or with hydroxy; $C_5$–$C_8$ alkenyl; $C_5$–$C_8$ cycloalkenyl optionally subsituted with $C_1$–$C_4$ alkyl; piperidyl N-substituted with $C_1$–$C_4$ alkyl; tetrahydrothiopyranyl or tetrahydropyranyl; and $R^3$ is H or $C_1$–$C_4$ alkyl optionally substituted with $C_1$–$C_4$ alkoxy or with hydroxy; or $R^2$ and $R^3$, together with the nitrogen atom to which they are attached, form a piperidine ring which is optionally substituted wiht $C^1$–$C^4$ alkyl or is optionally benzo-fused; are potent and selective thrombin inhibitors useful in the treatment of, inter alia, deep vein thrombosis; reocclusion following thrombolytic therapy; chronic arterial obstruction; peripheral vascular disease; acute myocardial infarction; unstable angina; atrial fibrillation; thrombotic stroke; transient ischaemic attacks; restenosis and occlusion following angiopasty; or neurodegenerative disorders.

9 Claims, No Drawings

ANTITHROMBOTIC N-AMIDINOPIPERIDINE AND BENZAMIDINE DERIVATIVES

This application was filed under 35 U.S.C. §371 based on PCT/EP96/04610, which was filed on Oct. 21, 1996 which claims priority from Great Britain application No. 9522495.2 which was filed on Nov. 2, 1998 and is now abandoned.

This invention relates to a series of N-amidinopiperidine and benzamidine derivatives, which are antithrombotic agents, having utility in a variety of therapeutic areas including the prevention and/or treatment of deep vein thrombosis (DVT) after surgery, major medical illness, paralysis, malignancy, prolonged immobilisation trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extra-corporeal circuits; occlusion of arterio-venous shunts and blood vessel grafts (including coronary artery by-pass grafts); and restenosis and occlusion following angioplasty. They also have utility as an adjunct to thrombolytic therapy.

The compounds of the invention are potent and selective inhibitors of thrombin, which is the final serine protease enzyme in the coagulation cascade. The prime function of thrombin is the cleavage of fibrinogen to produce fibrin which forms linear insoluble polymers which, in turn, are cross-linked by factor XIIIa, itself activated by thrombin. In addition, thrombin regulates its own production by activation of factors V and VIII earlier in the cascade. It also has important actions at the cellular level, where it acts on specific receptors to cause platelet aggregation, endothelial cell activation and fibroblast proliferation. Thus thrombin has a central regulatory role in haemostasis and thrombus formation.

Clearly then, potent, selective and orally bioavailable thrombin inhibitors represent an attractive target for the convenient therapeutic control of thrombosis. In addition, thrombin potently causes neurite retraction and therefore a thrombin inhibitor is of potential therapeutic utility in the treatment of acute and chronic neurodegenerative disorders. Furthermore, the compounds disclosed herein are of potential value in the treatment of inflammatory disorders and scarring, and in wound healing.

Because of their potential as substrate mimics, arginine derivatives have been explored as thrombin inhibitors and this work led to the discovery of argatroban (see Cardiovascular Drug Rev., 1991, 9, 247). In turn, other research groups have sought to express the basic arginine function in alternative structures; for example, WO-A-95/13274 discloses amidinophenylalanine and amidinopyridylalanine derivatives as antithrombotic agents. Further variations on the theme of arginine mimicry amongst thrombin inhibitors are represented by, inter alia, the guanidinyl- and amidinyl-substituted heterocyclic compounds disclosed in EP-A-0623595.

The compounds of the present invention are potent thrombin inhibitors, selective (in comparison with their inhibition of, for example, trypsin, plasmin, butyrylcholinesterase and elastase), well tolerated and orally bioavailable. Accordingly, the present invention provides a compound of formula (I):

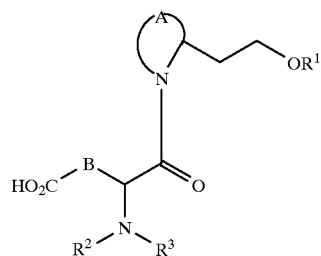

pharmaceutically acceptable salts thereof, and pharmaceutically acceptable solvates of either entity,
wherein A is optionally monounsaturated $C_4$–$C_5$ alkylene optionally substituted with $C_1$–$C_4$ alkyl;
B is $C_1$–$C_3$ alkylene optionally substituted with $C_1$–$C_4$ alkyl;
$R^1$ is N-amidino-4-piperidyl or 4-amidinophenyl;
$R^2$ is $C_4$–$C_{12}$ alkyl; ($C_3$–$C_8$ cycloalkyl)$C_1$–$C_4$ alkylene; optionally methylene-bridged $C_5$–$C_8$ cycloalkyl optionally substituted with one to three $C_1$–$C_4$ alkyl groups or with hydroxy; $C_5$–$C_8$ alkenyl;
$C_5$–$C_8$ cycloalkenyl optionally substituted with $C_1$–$C_4$ alkyl; piperidyl N-substituted with $C_1$–$C_4$ alkyl; tetrahydrothiopyranyl or tetrahydropyranyl;
and $R^3$ is H or $C_1$–$C_4$ alkyl optionally substituted with $C_1$–$C_4$ alkoxy or with hydroxy;
or $R^2$ and $R^3$, together with the nitrogen atom to which they are attached, form a piperidine ring which is optionally substituted with $C_1$–$C_4$ alkyl or is optionally benzo-fused.

In the above definition, unless otherwise indicated, alkyl and alkoxy groups having three or more carbon atoms and alkenyl groups having four or more carbon atoms may be straight-chain or branched-chain.

The compounds of formula (i) contain two or more asymmetric centres and thus can exist as stereoisomers, i.e. as enantiomers or as diastereoisomers as well as mixtures thereof.

The preferred stereoisomers are of formula (IA):

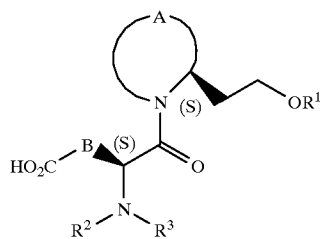

Also included in the invention are radiolabelled derivatives of compounds of formula (I) which are suitable for biological studies.

The pharmaceutically acceptable salts of the compounds of formula (I) are, for example, non-toxic acid addition salts formed with inorganic acids such as hydrochloric, hydrobromic, sulphuric and phosphoric acid, with organo-carboxylic acids, or with organo-sulphonic acids. Compounds of formula (I) can also provide pharmaceutically acceptable metal salts, in particular non-toxic alkali metal salts, with bases. Examples include the sodium and potassium salts.

A preferred group of compounds of formula (I) is that wherein A is butylene; B is $C_1$–$C_2$ alkylene; $R^2$ is $C_4$–$C_6$ alkyl; ($C_3$–$C_6$ cycloalkyl)$CH_2$; $C_5$–$C_8$ cycloalkyl optionally substituted with one to three methyl groups or with hydroxy; norbornyl; $C_6$–$C_7$ cycloalkenyl optionally substituted with methyl; piperidyl N-substituted with methyl; tetrahydrothiopyranyl or tetrahydropyranyl; $R^3$ is H, methyl or ethyl; or $R^2$ and $R^3$, together with the nitrogen atom to which they are attached, form a piperidine ring substituted with methyl; and $R^1$ is as previously defined for formula (I).

A more preferred group of compounds of formula (i) is that wherein A is butylene; B is methylene; $R^1$ is N-amidino-4-piperidyl; $R^2$ is 3-pentyl; ($C_5$–$C_6$ cycloalkyl)$CH_2$; cyclopentyl; cyclohexyl optionally substituted with one or two methyl groups; 2-hydroxycyclohexyl; 2-norbornyl; cycloheptyl; cyclooctyl; cyclohexenyl optionally substituted with methyl; cycloheptenyl; 3-tetrahydrothiopyranyl; 4-tetrahydrothiopyranyl or 3-tetrahydropyranyl; and $R^3$ is H, methyl or ethyl.

A most preferred group of compounds of formula (I) is that wherein A is butylene; B is methylene; $R^1$ is N-amidino-4-piperidyl; $R^2$ is cyclohexyl; 3-methylcyclohexyl; 3,3-dimethylcyclohexyl; 3,5-dimethylcyclohexyl; 2-norbornyl; cycloheptyl; cyclooctyl; 3-cyclohexenyl; 3-methyl-3-cyclohexenyl or 4-cycloheptenyl; and $R^3$ is H or methyl.

Particularly preferred individual compounds of the invention include:

N-(N-cycloheptyl-N-methyl-(S)-α-aspartyl)-2(S)-[2-(N-amidino-4-piperidyloxy)ethyl]piperidine;

N-(N-4-cycloheptenyl-N-methyl-(S)-α-aspartyl)-2(S)-[2-(N-amidino-4-piperidyloxy)ethyl]piperidine;

N-(N-methyl-N-3(R)-methylcyclohexyl-(S)-α-aspartyl)-2(S)-[2-(N-amidino-4-piperidyloxy)ethyl]piperidine; and N-(N-cyclohexyl-N-methyl-(S)-α-aspartyl)-2(S)-[2-(N-amidino-4-piperidyloxy)ethyl]piperidine;

and pharmaceutically acceptable salts thereof, and pharmaceutically acceptable solvates of either entity.

In another aspect, the present invention provides processes for the preparation of compounds of formula (I), their pharmaceutically acceptable salts, and pharmaceutically acceptable solvates of either entity.

A compound of formula (I) may be prepared from a compound of formula (II):

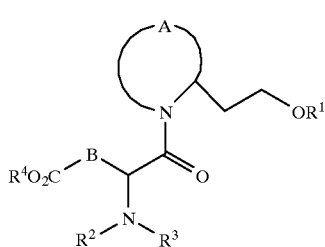

(II)

wherein $R^4$ is $C_1$–$C_4$ alkyl or benzyl, and A, B, $R^1$, $R^2$ and $R^3$ are as previously defined for formula (I). Depending on the nature of $R^4$, it may be removed by conventional acid- or base-catalysed hydrolysis, protonolysis or hydrogenolysis. In cases where the amidino group in $R^1$ is also protected, it is particularly convenient to remove the amidine protecting group ($P^1$) in the same reaction step as the removal of $R^4$; $P^1$ may be a typical amine protecting group such as t-butoxycarbonyl (Boc) or benzyloxycarbonyl (Cbz).

A preferred method of preparing a compound of formula (I) wherein $R^1$ is N-amidino-4-piperidyl is by single step deprotection of a compound of formula (IIA):

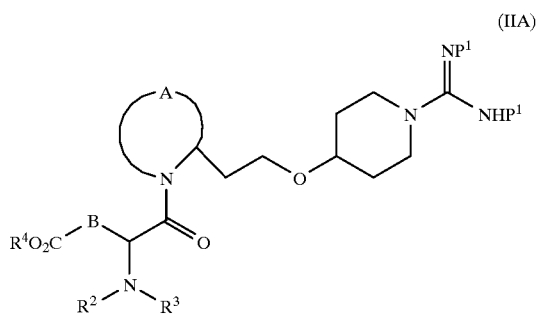

(IIA)

wherein $R^4$ and $P^1$ are removable under the same reaction conditions. Preferably $R^4$ is t-butyl, $P^1$ is Boc and the reaction is effected by protonolysis using, for example, hydrogen chloride or trifluoroacetic acid at from about 0° C. to about room temperature. Typically, a solution of a compound of formula (IIA) in a suitable solvent such as dichloromethane is saturated with hydrogen chloride at about 0° C. and then allowed to warm to room temperature. Full deprotection is normally complete within 2 to 6 hours at room temperature.

Alternatively, a 1:1 mixture of trifluoroacetic acid and a suitable solvent such as dichloromethane may be employed as the reaction medium at from about 0° C. to about room temperature.

A preferred method of preparing a compound of formula (I) wherein $R^1$ is 4-amidinophenyl is by hydrolysis of the corresponding ester of formula (IIB):

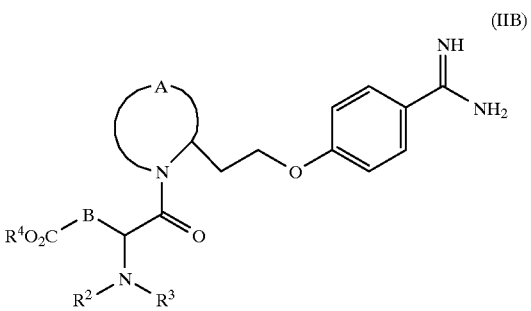

(IIB)

wherein $R^4$ is typically ethyl and/or benzyl. The reaction may be acid- or base-catalysed, but is generally carried out using an alkali metal hydroxide such as sodium or potassium hydroxide in aqueous solution, optionally in the presence of a suitable cosolvent, at from about room temperature to about 100° C. Preferred conditions are the use of aqueous sodium hydroxide solution, with 1,4-dioxan as cosolvent, at about room temperature.

Thus novel intermediates of formula (II) wherein the amidino group in $R^1$ is optionally protected and A, B, $R^1$, $R^2$, $R^3$ and $R^4$ are as previously defined for formula (II) also form part of the invention.

A compound of formula (IIA) may be prepared from a compound of formula (III):

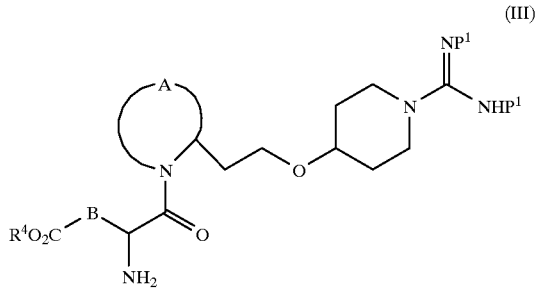

wherein A, B, $R^4$ and $P^1$ are as previously defined for formula (II), by conventional alkylation of the primary amino group. When $R^3$ is not H, two separate N-alkylation steps are required, generally with $R^2$ being introduced first. Only when $R^2$ and $R^3$ are identical, i.e. $C_4$ alkyl, may the two alkylations being carried out in a single step. Similarly, when $R^3$ and the piperidyl N-substituent of $R^2$ are identical, i.e. $C_1$–$C_4$ alkyl, these may be introduced in a single step. When $NR^2R^3$ forms a piperidine ring; the required bis-alkylation is preferably effected in a single step.

Of the plethora of N-alkylation procedures available, one example of a general reaction which may be employed is that of a compound of formula (III) with a compound of formula $R^2X$, wherein $R^2$ is as previously defined for formula (II), and X is a suitable leaving group, e.g. halo (preferably chloro, bromo or iodo), $C_1$–$C_4$ alkanesulphonyloxy, trifluoromethanesulphonyloxy or arylsulphonyloxy (preferably benzenesulphonyloxy or p-toluenesulphonyloxy), in the presence of an appropriate base, e.g. the carbonate or bicarbonate salt of an alkali or alkaline earth metal, or a tertiary amine, in a suitable solvent such as a $C_1$–$C_4$ alkanol, 1,2-dimethoxyethane, acetonitrile, dimethylformamide or N,N-dimethylacetamide, optionally in the presence of sodium or potassium iodide. The reaction may be conducted at from about 0° C. to about 150° C., preferably at from about room temperature to about 85° C.

If appropriate, a conventional amine protecting group strategy may be used for the introduction of $R^2$.

$R^3$, when not H, may then be similarly introduced. When $R^3$ is $C_2$–$C_4$ alkyl substituted with hydroxy, it may be convenient to react a compound of formula (III) with an appropriate epoxide-containing $R^3$ precursor, optionally in the presence of a tertiary amine base, e.g. triethylamine, and preferably in a suitable solvent such as a $C_1$–$C_4$ alkanol. The reaction can be conducted at from about 0° C. to about 150° C., preferably at from room temperature to about 60° C. using methanol as solvent. When $R^3$ is 2-hydroxyethyl, an ethylene oxide equivalents is preferably employed. Thus a compound of formula (III) may be reacted with ethylene carbonate in a suitable solvent such as dimethylformamide at about 120° C.

Alternatively, as a further example of a general N-alkylation reaction, the desired transformation may be achieved by reductive alkylation of a compound of formula (III) using the appropriate aldehyde- or ketone-containing $R^2$ precursor. The substrate of formula (III) and carbonyl reagent may be reacted together under conventional catalytic hydrogenation conditions or in the presence of sodium cyanoborohydride or sodium triacetoxyborohydride, in a suitable solvent such as methanol, ethanol, dichloromethane, 1,2-dichloroethane or tetrahydrofuran, optionally in the presence of glacial acetic acid or in the presence of pre-activated molecular sieves, at about room temperature.

Preferably, a compound of formula (III) is treated initially with from 1.1 to 2.0 molecular equivalents of the appropriate aldehyde or ketone, optionally in the presence of from 1.0 to 2.1 molecular equivalents of glacial acetic acid or in the presence of pre-activated 4A molecular sieves, in tetrahydrofuran or 1,2-dichloroethane, at about room temperature followed, about 5 minutes later, with from 1.4 to 2.0 molecular equivalents of sodium triacetoxyborohydride.

$R^3$, when not H, may be similarly introduced subsequently, although up to about 3 molecular equivalents of the appropriate aldehyde or ketone and of sodium triacetoxyborohydride may be required to effect a reasonable conversion. When $R^3$ is methyl, it is particularly convenient to use about 4 molecular equivalents of aqueous formaldehyde solution and about 2 molecular equivalents of sodium triacetoxyborohydride in dichloromethane at about room temperature. When both $R^3$ and the piperidyl N-substituent of $R^2$ are methyl, about 5 molecular equivalents of aqueous formaldehyde solution may be more desirable. When $NR^2R^3$ forms a piperidine ring, a compound of formula (III) may be treated initially with about 1.5 molecular equivalents of the appropriate glutaraldehyde followed, about 0.5 hour later, with about 1 molecular equivalent of sodium triacetoxyborohydride at about room temperature.

A compound of formula (III) may be prepared from a compound of formula (IV):

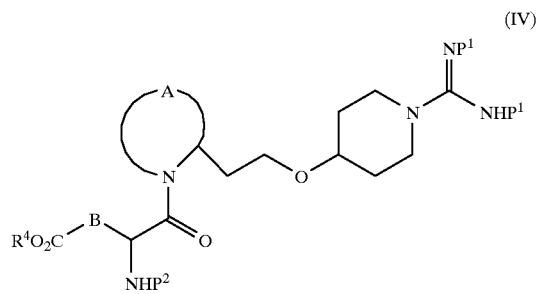

wherein $P^2$, like $P^1$ is a typical amine protecting group and A, B, $R^4$ and $P^1$ are as previously defined for formula (III), with the proviso that $P^2$ is selectively removable in the presence of P and $R^4$; preferably $P^2$ is 9-fluorenylmethoxycarbonyl (Fmoc). The particular protecting group can be removed under standard conditions which, in the case of Fmoc, are treatment with about a 10-fold excess of piperidine in a suitable solvent such as tetrahydrofuran at about room temperature.

A compound of formula (IV) may be prepared by coupling a compound of formula (V):

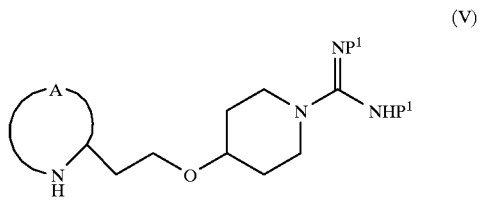

wherein A and $P^1$ are as previously defined for formula (IV), with a compound of formula (VI):

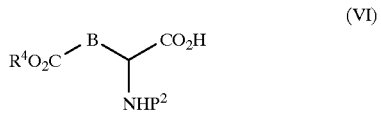

(VI)

wherein B, $R^4$ and $P^2$ are as previously defined for formula (IV). The coupling reaction may be achieved using conventional amide bond-forming techniques, in particular any one of a host of amino acid coupling variations. For example, the acid of formula (VI) may be activated using a carbodiimide such as 1,3-dicyclohexylcarbodiimide or 1-ethyl-3-(3-dimethylamino-1-propyl)carbodiimide optionally in the presence of 1-hydroxybenzotriazole and/or a catalyst such as 4-dimethylaminopyridine, or by using a halotrisaminophosphonium salt such as bromotris(pyrrolidino)phosphonium hexafluorophosphate. Either type of coupling is conducted in a suitable solvent such as dichloromethane, optionally in the presence of a tertiary amine such as N-methyimorpholine or N-ethyidiisopropylamine (for example when either the compound of formula (V) or the activating reagent is presented in the form of an acid addition salt), at about 0° C. Preferably, from 1.1 to 2.0 molecular equivalents of the activating reagent and from 2.0 to 3.0 molecular equivalents of any tertiary amine present are employed.

A compound of formula (V) may be prepared from a compound of formula (VII):

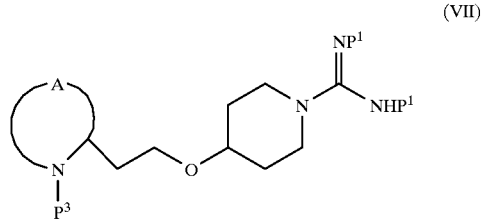

(VII)

wherein $P^3$, like $P^1$ and $P^2$, is a typical amine protecting group and A and $P^1$ are as previously defined for formula (V), with the proviso that $P^3$ is selectively removable in the presence of $P^1$; preferably $P^3$ is benzyloxycarbonyl (Cbz). The particular protecting group can be removed under standard conditions which, in the case of Cbz, are hydrogenolysis in the presence of an appropriate catalyst in a suitable solvent. Preferably the deprotection is effected using a palladium on charcoal catalyst and ethanol as solvent.

A compound of formula (VII) may be prepared from a compound of formula (VIII):

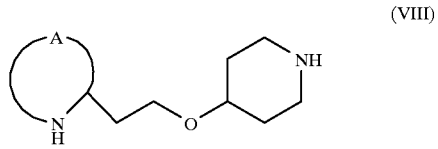

(VIII)

wherein A and $P^3$ are as previously defined for formula (VII), by reaction with a S-alkylisothiourea derivative of formula (IX):

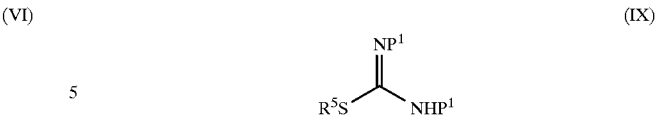

(IX)

wherein $R^5$ is $C_1$–$C_3$ alkyl and P is as previously defined for formula (VII), in a suitable solvent such as dichloromethane, optionally in the presence of a mercury(II) salt and a tertiary amine, at from about 0° C. to about 40° C. Preferably, $R^5$ is methyl, a 10% excess of the compound of formula (IX) is used, and the reaction is carried out in the presence of I molecular equivalent of mercuric chloride and a 2-fold excess of triethylamine.

A compound of formula (VIII) may be prepared from a compound of formula (X):

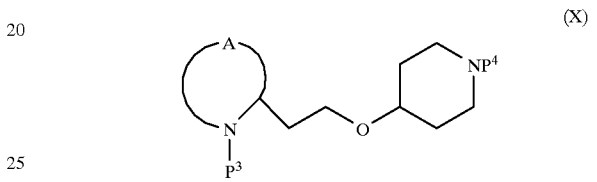

(X)

wherein $P^4$, like $P^1$, $P^2$ and $P^3$, is a typical amine protecting group and A and $P^3$ are as previously defined for formula (VIII), with the proviso that $P^4$ is selectively removable in the presence of $P^3$; preferably $P^4$ is t-butoxycarbonyl (Boc). The particular protecting group can be removed under standard conditions which, in the case of Boc, are as described previously for the conversion of a compound of formula (IIA) to a compound of formula (I).

A compound of formula (X) may be prepared by reaction of a compound of formula (XI):

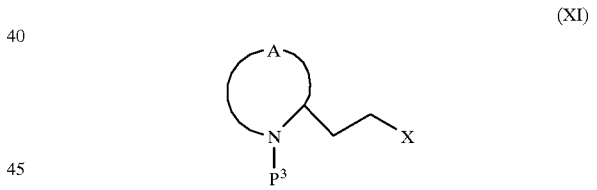

(XI)

wherein X is a suitable leaving group as previously defined and A and $P^3$ are as previously defined for formula (X), with the anion of a compound of formula (XII):

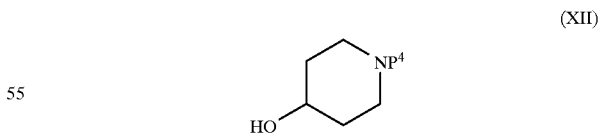

(XII)

wherein $P^4$ is as previously defined for formula (X), under conditions similar to those described previously for the alkylation of a compound of formula (III) with $R^2X$. Preferably, X is methanesulphonyloxy, the anion of a compound of formula (XII) is generated using sodium hydride, the solvent is dimethylformamide and the O-alkylation is conducted at about room temperature.

A compound of formula (XI) may be prepared from a compound of formula (XIII):

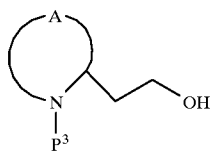

(XIII)

wherein A and P³ are as previously defined for formula (XI), by standard procedures. For example, when X is methanesulphonyloxy, by treatment of a compound of formula (XIII) with about 2 molecular equivalents of methanesulphonyl chloride in the presence of about 2 molecular equivalents of a tertiary amine, e.g. triethylamine, in a suitable solvent such as dichloromethane at from about 0° C. to about 17° C.

A compound of formula (XIII) may also be prepared by standard procedures from a compound of formula (XIV):

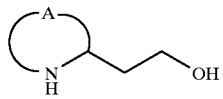

(XIV)

wherein A is as previously defined for formula (XIII). For example, when P³ is Cbz, by treatment of a compound of formula (XIV) with about a 5% excess of N-(benzyloxycarbonyloxy)succinimide in the presence of about a 10% excess of a tertiary amine, e.g. triethylamine, in a suitable solvent such as dichloromethane at from about 0° C. to about room temperature.

The preferred S-enantiomer of a compound of formula (XIV) may be obtained therefrom by classical resolution procedures (see, for example, Rec. Trav. chim., 1971, 90 755) or by chromatographic resolution procedures using either a chiral auxiliary or a chiral stationary phase. Alternatively, de novo asymmetric synthetic methodology may be adopted.

A compound of formula (IIB) may be prepared from a compound of formula (XV):

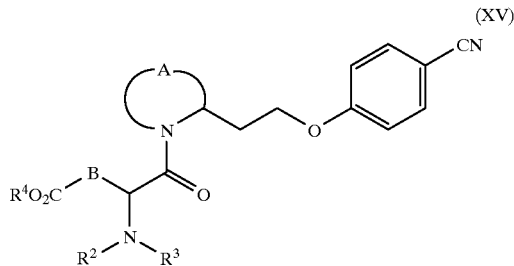

(XV)

wherein A, B, R², R³ and R⁴ are as previously defined for formula (II); preferably R⁴ is benzyl. This may be achieved by conversion of the nitrile group to the required amidine via an intermediate imino ether under conventional conditions. For example, a solution of a compound of formula (XV) in a lower alkanol such as ethanol is saturated with hydrogen chloride at about 0° C. to generate the imino ether hydrochloride which, in turn, is treated as a solution in the same alcohol with excess ammonia at about 50° C. followed by heating of the resulting mixture under reflux. The amidine may be conveniently isolated as an acid addition salt, e.g. hydrochloride, if necessary.

Alternatively, the imino ether free base may be generated in situ by treatment of the nitrile with the appropriate alkali metal alkoxide in the corresponding lower alkanol as solvent at about room temperature; for example, sodium ethoxide in ethanol. This step is followed by treatment of the imino ether solution with a suitable ammonium salt, e.g. ammonium chloride, at about room temperature.

A compound of formula (XV) may be prepared from a compound of formula (XVI):

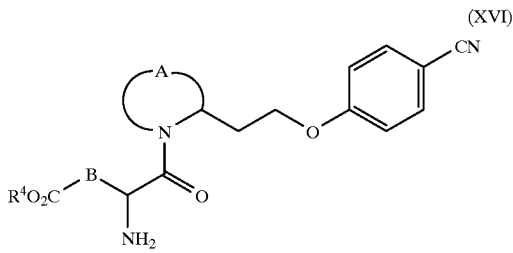

(XVI)

wherein A, B and R⁴ are as previously defined for formula (XV), by analogy with the methods described previously for the conversion of a compound of formula (III) to a compound of formula (IIA).

A compound of formula (XVI) may be prepared from a compound of formula (XVII):

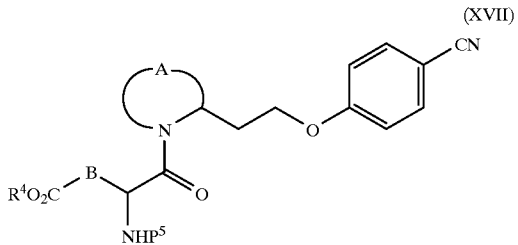

(XVII)

wherein P⁵ is a typical amine protecting group and A, B and R⁴ are as previously defined for formula (XVI), with the proviso that P⁵ is selectively removable in the presence of R⁴; preferably P⁴ is t-butoxycarbonyl (Boc). The particular protecting group can be removed under standard conditions which, in the case of Boc, are as described previously for the conversion of a compound of formula (IIA) to a compound of formula (I), but with the modification that the deprotection is conducted in the presence of about 2 molecular equivalents of anisole. Typically, the reaction is carried out using excess trifluoroacetic acid as reagent and dichloromethane as solvent at about 0° C.

A compound of formula (XVII) may be prepared by coupling a compound of formula (XVIII):

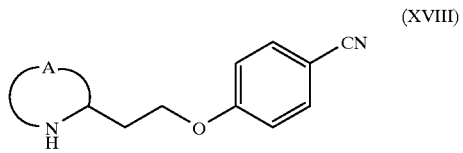

(XVIII)

wherein A is as previously defined for formula (XVII), with a compound of formula (XIX):

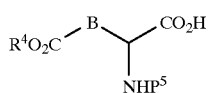

(XIX)

wherein B, $R^4$ and $P^5$ are as previously defined for formula (XVII), by analogy with the methods described previously for the conversion of compounds of formulae (V) and (VI) to a compound of formula (IV).

A compound of formula (XVIII) may be prepared from a compound of formula (XX):

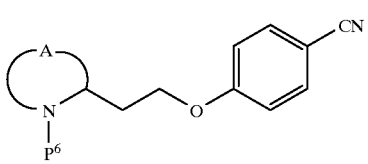

(XX)

wherein $P^6$ is a typical amine protecting group and A is as previously defined for formula (XVIII); preferably $P^6$ is Boc. The particular protecting group can be removed under standard conditions which, in the case of Boc, are as described previously for the conversion of a compound of formula (XVII) to a compound of formula (XVI).

A compound of formula (XX) may be prepared from a compound of formula (XXI):

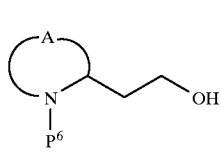

(XXI)

wherein A and $P^6$ are as previously defined for formula (XX), and 4-cyanophenol by analogy with the methods described previously for the conversion of a compound of formula (XIII) to a compound of formula (X).

However, a more convenient strategy is to exploit the Mitsunobu reaction whereby a compound of formula (XXI) and 4-cyanophenol can be coupled directly. Typically, about a 10% excess of a di($C_1$–$C_3$ alkyl) azodicarboxylate is added to a mixture of the two components, preferably with the phenol also in about a 10% excess, in a suitable solvent such as dichloromethane at about 0° C., followed by removal of the cooling bath.

A compound of formula (XXI) may be prepared from a compound of formula (XIV) as described previously for the conversion of a compound of formula (XIV) to a compound of formula (XIII). For example, when $P^6$ is Boc, by treatment of a compound of formula (XIV) with di-t-butyl dicarbonate in a suitable solvent such as ethyl acetate at from about 0° C. to about room temperature.

The intermediates required for the introduction of $R^2$ and $R^3$ (when not H), when neither commercially available nor subsequently described, can be obtained either by analogy with the processes described in the Preparations section or by conventional synthetic procedures, in accordance with standard textbooks on organic chemistry or literature precedent, from readily accessible starting materials using appropriate reagents and reaction conditions.

Moreover, persons skilled in the art will be aware of variations of, and alternatives to, those processes described hereinafter in the Examples and Preparations sections which allow the compounds defined by formula (I) to be obtained.

The pharmaceutically acceptable acid addition salts of the compounds of formula (I) may also be prepared in a conventional manner. For example a solution of the free base is treated with the appropriate acid, either neat or in a suitable solvent, and the resulting salt isolated either by filtration or by evaporation under reduced pressure of the reaction solvent. Pharmaceutically acceptable base addition salts can be obtained in an analogous manner by treating a solution of a compound of formula (I) with the appropriate base. Both types of salt may be formed or interconverted using ion-exchange resin techniques.

The biological activities of the compounds of the present invention were determined by the following test methods.

Chromogenic Assays

The inhibition of thrombin, trypsin, plasmin or factor Xa is measured in 96 well plate chromogenic assays. The percentage inhibition and $IC_{50}$ are calculated from triplicate samples of an 8 concentration dose-response curve. From the substrate Km and $IC_{50}$, the Ki for each inhibitor is calculated. All assays are carried out in a total incubation of 200 $\mu$l of 50 mM HEPES and 150 mM NaCl at pH 8.0, and all compound dilutions are preincubated with enzyme at room temperature for 15 minutes prior to addition of substrate. After 30 minutes incubation at 30° C., the O.D. is measured at 405 nM in a 96 well plate reader. Thrombin activity is measured using bovine thrombin and S2238 (H-D-Phe-Pip-Arg-pNA), bovine pancreatic trypsin is assayed with S2222 (Benz-Isoleu-Glu-Gly-Arg-pNA), bovine plasma plasmin is assayed with Chromozym PL (Tosyl-Giy-Pro-Lys-pNA) and bovine factor Xa is assayed in 50 mM Tris, 150 mM NaCl, pH 7.5 buffer with S2222.

Clotting Assays

Thrombin time (TT) and activated partial thromboplastin time (APTT) are measured using Instrumentation Laboratories (IL) Test TT reagent and IL Test APTT (ellagic acid) reagent respectively in an Automated Coagulation Laboratory (ACL), according to the manufacturer's instructions.

In Vitro

To 1 ml aliquots of rat pooled plasma (citrated), a 1/100 volume of a range of compound concentrations is added and the resulting mixtures preincubated at room temperature for 15 minutes, after which the TT and APTT are measured.

Ex Vivo

Compounds are dosed per os, intravenously or intraduodenally to rats. Pre- and post-dose blood samples are taken into citrate solution and plasma prepared. TT and APTT are measured as for in vitro assays.

In therapy, the compounds of formula (I), their pharmaceutically acceptable salts, and pharmaceutically acceptable solvates of either entity, can be administered alone, but will generally be administered in admixture with a pharmaceutical carrier selected with regard to the intended route of administration and standard pharmaceutical practice. Preferably, they are administered orally in the form of tablets containing such excipients as starch or lactose, or in capsules or ovules either alone or in admixture with excipients, or in the form of elixirs, solutions or suspensions containing flavouring or colouring agents. They can also be injected parenterally, for example intravenously, intramuscularly or subcutaneously. For parenteral administration, they are best used in the form of a sterile aqueous solution which may contain other substances, for example enough salts or glucose to make the solution isotonic with blood. For buccal or sublingual administration they may be administered in the form of tablets or lozenges which can be formulated in a conventional manner.

For oral, parenteral, buccal and sublingual administration to patients, the daily dosage level of the compounds of formula (I) and their pharmaceutically acceptable salts and solvates will be from 1 to 1000 mg (in single or divided doses). Thus tablets or capsules may contain from 0.5 to 500 mg of active compound for administration singly, or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited and such are within the scope of this invention.

Thus the invention provides a pharmaceutical composition comprising a compound of formula (I), or a pharmaceutically acceptable salt thereof, or a pharmaceutically acceptable solvate of either entity, together with a pharmaceutically acceptable diluent or carrier.

The invention also provides a compound of formula (I), or a pharmaceutically acceptable salt thereof, or a pharmaceutically acceptable solvate of either entity, or a pharmaceutical composition containing any of the foregoing, for use as a medicament.

The invention further includes the use of a compound of formula (I), or a pharmaceutically acceptable salt thereof, or a pharmaceutically acceptable solvate of either entity, or a pharmaceutical composition containing any of the foregoing, for the manufacture of a medicament for the curative or prophylactic treatment of deep vein thrombosis (DVT) after surgery, major medical illness, paralysis, malignancy, prolonged immobilisation trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extracorporeal circuits; occlusion of arterio-venous shunts and blood vessel grafts (including coronary artery by-pass grafts); restenosis and occlusion following angioplasty; neurodegenerative disorders; inflammatory disorders; or scarring.

In a further aspect, the invention provides a method of treating a mammal (including a human being) to cure or prevent deep vein thrombosis (DVT) after surgery, major medical illness, paralysis, malignancy, prolonged immobilisation trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extra-corporeal circuits; occlusion of arterio-venous shunts and blood vessel grafts (including coronary artery by-pass grafts); restenosis and occlusion following angioplasty; neurodegenerative disorders; inflammatory disorders; or scarring; which comprises treating said mammal with an effective amount of a compound of formula (I), or a pharmaceutically acceptable salt thereof, or a pharmaceutically acceptable solvate of either entity, or a pharmaceutical composition containing any of the foregoing.

The syntheses of the compounds of the invention and of the intermediates f or us e therein are illustrated by the following Examples and Preparations. The purity (Rf) of the compounds was routinely monitored by thin layer chromatography using Merck Kieselgel 60 $F_{254}$ plates and the following solvent systems (SS):

1. isobutyl methyl ketone:glacial acetic acid:water, 2:1:1 (upper phase);
2. hexane:ethyl acetate, 1:1;
3. hexane:ethyl acetate, 7:3;
4. dichloromethane:methanol:0.880 aqueous ammonia, 85:15:2;
5. dichloromethane:methanol:0.880 aqueous ammonia, 84:14:2;
6. hexane:ethyl acetate, 6:4;
7. dichloromethane:methanol:0.880 aqueous ammonia, 93:7:1;
8. dichloromethane:methanol, 90:10;
9. dichloromethane:methanol:0.880 aqueous ammonia, 93:7:2;
10. dichloromethane:methanol:0.880 aqueous ammonia, 90:10:1;
11. dichloromethane:methanol, 95:5;
12. dichloromethane:methanol:0.880 aqueous ammonia, 193:7:1;
13. ethyl acetate;
14. hexane:ether, 1:1;
15. hexane:ether, 1:3;
16. dichloromethane:methanol:0.880 aqueous ammonia, 80:20:5;
17. chloroform:methanol, 95:5;
18. hexane:ethyl acetate, 3:7;
19. methanol:ethyl acetate:glacial acetic acid:0.880 aqueous ammonia:water, 60:12:4:4:8.

$^1$H Nuclear magnetic resonance (NMR) spectra were recorded using either a Nicolet QE-300 or a Bruker AC-300 spectrometer and were in all cases consistent with the proposed structures.

Mass spectra were obtained with a Fisons Instrument Trio 1000 spectrometer using thermospray ionisation.

Room temperature means 20–25° C.

EXAMPLE 1

N-[N-(3-Methyl-3-cyclohexenyl)-(S)-α-asrpartyl]-2 (S)-[2-(N-amidino-4-piperidyloxy)ethyl]piperidine dihydrochloride A stirred, ice-cooled solution of the title compound of Preparation 20 (111 mg, 0.54 mmol) in dichloromethane (10 ml) was saturated with hydrogen chloride, the cooling bath removed and the resulting solution stirred at room temperature until total deprotection was complete: (typically 2 to 6 hours at room temperature). Evaporation under reduced pressure gave the title compound (76 mg) as a white foam. Rf 0.60 (SS 19). Found: C,46.98; H,8.11; N, 11.13. $C_{24}H_{41}N_5O_4$; 2HCl; 3H$_2$O; 0.40 CH$_2$Cl$_2$ requires C,46.92; H,8.04; N,11.21%

EXAMPLE 2

N-[N-(N-Methyl-3-piperidyl)-(S) α-aspartyl]-2(S)-[2-(N-amidino-4-piperidyloxy)ethyl]piperidine trihydrochloride Obtained from the title compound of Preparation 22 by analogy with Example 1. Rf 0.18 (SS 19). Found: C,41.13; H,7.29; N,12.26. $C_{23}H_{42}N_6O_4$; 3HCl; 1.50 H$_2$O; 1.20 CH$_2$Cl$_2$ requires C,41.23; H,7.21; N,11.92%. m/e 467.5 (M+H)$^+$.

EXAMPLE 3

N-[N-(2-Norbornyl)-(S)α-aspartyl]-2(S)-[2-(N-amidino-4-piperidyloxy)ethyl]piperidine dihydrochloride Obtained from the title compound of Preparation 23 by analogy with Example 1. Rf 0.52 (SS 19). Found: C,49.78; H,8.02; N,11.97. $C_{24}H_{41}N_5O_4$; 2HCl; $H_2O$; 0.40 $CH_2Cl_2$ requires C,49.80; H,7.84; N,11.90%. m/e 464.3 $(M+H)^+$.

EXAMPLE 4

N-(N-Cyclopentylmethyl-(S)-α-aspartyl)-2(S)-[2-(N-amidino-4-piperidyloxy)-ethyl]piperidine dihydrochloride Obtained from the title compound of Preparation 39 by analogy with Example 1. Rf 0.56 (SS 19). Found: C,48.61; H,7.94; N,12.07. $C_{23}H_{41}N_5O_4$; 2HCl; 1.50 $H_2O$; 0.33 $CH_2Cl_2$ requires C,48.35; H,8.11; N,12.08%. m/e 452 $(M+H)^+$.

EXAMPLE 5

N-[N-(cis-3,5-Dimethylcyclohexyl)-(S)-α-aspartyl]-2(S)-[2-(N-amidino-4-piperidyloxy)ethyl]piperidine dihydrochloride Obtained from the title compound of Preparation 30 (diastereoisomer A) by analogy with Example 1. Rf 0.59 (SS 19). Found: C,50.10; H,8.24; N,11.24. $C_{25}H_{45}N_5O_4$; 2HCl; 2.30 $H_2O$; 0.10 $CH_2Cl_2$ requires C,50.04; H,8.67; N,11.62%. m/e 480 $(M+H)^+$.

EXAMPLE 6

N-[N-(cis-3,5-Dimethylcyclohexyl)-(S)-α-aspartyl]-2(S)-[2-(N-amidino-4-piperidyloxy)ethyl]piperidine dihydrochloride Obtained from the title compound of Preparation 30 (diastereoisomer B) by analogy with Example 1. Rf 0.59 (SS 19). Found: C,49.69; H,8.54; N,11.19. $C_{25}H_{45}N_5O_4$; 2HCl; 2.50 $H_2O$; 0.10 $CH_2Cl_2$ requires C,49.74; H,8.68; N,11.55%. m/e 480 $(M+H)^+$.

EXAMPLE 7

N-[N-(3,3-Dimethylcyclohexyl)-(S)-α-aspartyl]-2(S)-[2-(N-amidino-4-piperidyloxy)ethyl]piperidine dihydrochloride Obtained from the title compound of Preparation 27 by analogy with Example 1. Rf 0.59 (SS 19). Found: C,50.27; H,8.75; N,11.53. $C_{25}H_{45}N_5O_4$; 2HCl; 2$H_2O$; 0.15 $CH_2Cl_2$ requires C,50.23; H,8.60; N,11.65%. m/e 480 $(M+H)^+$.

EXAMPLE 8

N-(N-Cycloheptyl-(S)-α-aspartyl)-2(S)-[2-(N-amidino-4-piperidyloxy)ethyl]piperidine dihydrochloride Obtained from the title compound of Preparation 31 by analogy with Example 1. Rf 0.50 (SS 19). Found: C,48.45; H,8.21; N,11.21. $C_{24}H_{43}N_5O_4$; 2HCl; 1.10 $H_2O$; 0.60 $CH_2Cl_2$ requires C,48.49; H,8.01; N,1 1.49%. m/e 466.5 $(M+H)^+$.

EXAMPLE 9

N-[N-(N-Methyl-4-piperidyl)-(S)-α-aspartyl]-2(R,S)-[2-(N-amidino4-piperidyloxy)ethyl]piperidine trihydrochloride Obtained from the title compound of Preparation 19 by analogy with Example 1. Rf 0.13 (SS 19). Found: C,43.79; H,7.59; H,12.43. $C_{23}H_{42}N_6O_4$; 3HCl; 1.40 $H_2O$; 0.60 $CH_2Cl_2$ requires C,43.46; H,7.57; N,12.89%. m/e 467.5 $(M+H)^+$.

EXAMPLE 10

N-(N-Cyclohexylmethyl-(S)-α-aspartyl)-2(R,S)-[2-(N-amidino-4-piperidyloxy)ethyl]piperidine dihydrochloride Obtained from the title compound of Preparation 38 by analogy with Example 1. Rf 0.56 (SS 19). Found: C,48.80; H,8.29; N,11.48. $C_{24}H43N_5O_4$; 2HCl; 1.50 $H_2O$; 0.40 $CH_2Cl_2$ requires C,48.88; H,8.20; N, 11.68%. m/e 466 $(M+H)^+$.

EXAMPLE 11

N-(N-Cyclohexyl-(S)-α-aspartyl)-2(R,S)-[2-(N-amidino-4-piperidyloxy)ethyl]piperidine dihydrochloride Obtained from the title compound of Preparation 25 by analogy with Example 1. Rf 0.57 (33 19). Found: C,47.51; H,7.75; N,11.62. $C_{23}H_{41}N_5O_4$; 2HCl; $CH_2Cl_2$ requires C,47.28; H,7.44; N,11.49%.

EXAMPLE 12

N-[N-(4-Tetrahydropyranyl)-(S)-α-aspartyl]-2(R,S)-[2-(N-amidino-4-piperidyloxy)ethyl]piperidine dihydrochloride Obtained from the title compound of Preparation 26 by analogy with Example 1. Rf 0.48 (SS 19). Found: C,44.44; H,7.27; N,11.15. $C_{22}H_{39}N_5O_5$; 2HCl; 0.50 $H_2O$; $CH_2Cl_2$ requires C,44.53; H,7.15; N,11.29%. m/e 454 $(M+H)^+$.

EXAMPLE 13

N-[N-(3.3-Dimethylcyclohexyl)-(S)-α-aspartyl]-2(R,S)-[2-( N-amidino-4-piperidyloxy)ethyl]piperidine dihydrochloride Obtained from the title compound of Preparation 28 by analogy with Example 1. Rf 0.60 (SS 19). Found: C,49.10; H,8.24; N,11.17. $C_{25}H_{45}N_5O_4$; 2HCl; $H_2O$; 0.67 $CH_2Cl_2$ requires C,49.18; H,8.09; N,11.18%. m/e 480 $(M+H)^+$.

EXAMPLE 14

N-(N-Cyclopentyl-(S)-α-aspartyl)-2(R,S)-[2-(N-amidino-4-piperidyloxy)-ethyl]piperidine dihydrochloride Obtained from the title compound of Preparation 33 by analogy with Example 1. Rf 0.44 (SS 19). Found: C,46.53; H,7.88; N,11.82. $C_{22}H_{39}N_5O_4$; 2HCl; 1.50 $H_2O$; 0.50 $CH_2Cl_2$ requires C,46.60; H,7.82; N,12.97%. m/e 438 $(M+H)^+$.

EXAMPLE 15

N-(N-Cycloheptyl-(S)-α-aspartyl]-2(R,S)-[2-(N-amidino-4-piperidyloxy)ethyl]piperidine dihydrochloride Obtained from the title compound of Preparation 32 by analogy with Example 1. Rf 0.49 (SS 19). Found: C,47.42; H,8.07; N,11.29. $C_{24}H_{43}N_5O_4$; 2HCl; 1.25 $H_2O$; 0.75 $CH_2Cl_2$ requires C,47.58; H,7.91; N,1 1.21%. m/e 466 $(M+H)^+$.

EXAMPLE 16

N-(N-Cyclooctyl-(S)-α-aspartyl)-2(R,S)-[2-(N-amidino-4-piperidyloxy)ethyl]piperidine dihydrochloride Obtained from the title compound of Preparation 34 by analogy with Example 1. Rf 0.58 (SS 19). Found: C,49.60; H,8.56; N,11.19. $C_{25}H_{45}N_5O_4$; 2HCl; 2H$_2$O; 0.25 CH$_2$Cl$_2$ requires C,49.73; H,8.51; N,11.48%.

EXAMPLE 17

N-[N-(2-Hydroxycyclohexyl)-(S)-α-aspartyl]-2(R,S)-[2-(N-amidino-4-Piperidyloxy)ethyl]piperidine bis-trifluoroacetate Obtained from the title compound of Preparation 35 by treatment with a 1:1 mixture of trifluoroacetic acid and dichloromethane (200 μl) for 3 hours at room temperature, followed by evaporation of the reaction mixture, to provide 0.37 mg. m/e 426.4 $(M-C(NH)NH_2+H)^+$.

EXAMPLE 18

N-[N-(3-Tetrahydrothiopyranyl)-(S)-α-aspartyl]-2(R,S)-[2-(N-amidino-4-piperidyloxy)ethyl]piperidine bis-trifluoroacetate Obtained from the title compound of Preparation 36 by analogy with Example 17 to provide 0.39 mg. m/e 428.3 $(M-C(NH)NH_2+H)^+$.

EXAMPLE 19

N-[N-(4-Tetrahydrothiopyranyl)-(S)α-aspartyl]-2(R,S)-[2-(N-amidino-4-piperidyloxy)ethyl]piperidine bis-trifluoroacetate Obtained from the title compound of Preparation 37 by analogy with Example 17 to provide 2 mg.

EXAMPLE 20

N-(N-Cyclohexyl-(S)-α-glutamyl)-2(R,S)-[2-(N-amidino-4-piperidyloxy)ethyl]piperidine dihydrochloride Obtained from the title compound of Preparation 52 by analogy with Example 1. Rf 0.49 (SS 19). Found: C,48.53; H,7.63; N,11.40. $C_{24}H_{43}N_5O_4$; 2HCl; H$_2$O; 0.65 CH$_2$Cl$_2$ requires C,48.40; H,7.96; N,11.45%. m/e 466 $(M+H)^+$.

EXAMPLE 21

N-[N-Methyl-N-(cis-3,5-dimethylcyclohexyl)-(S)-α-aspartyl]-2(S)-[2-(N-amidino-4-piperidyloxy)ethyl]piperidine dihyhdrochloride Obtained from the title compound of Preparation 45 by analogy with Example 1. Rf 0.61 (SS 19). Found: C,50.39; H,8.57; N,11.39. $C_{26}H_{47}N_5O_4$; 2HCl; 1.50 H$_2$O; 0.40 CH$_2$Cl$_2$ requires C,50.52; H,8.48; N, 1.16%. m/e 494 $(M+H)^+$.

EXAMPLE 22

N-(N-Cyclohexyl-N-methyl-(S)-α-aspartyl)-2(S)-[2-(N-amidino-4-piperidyloxy)ethyl]piperidine dihydrochloride Obtained from the title compound of Preparation 40 by analogy with Example 1. Rf 0.50 (SS 19). Found: C,47.31; H,8.02; N,10.74. $C_{24}H_{43}N_5O_4$; 2HCl; 1.30 H$_2$O; 0.80 CH$_2$Cl$_2$ requires C,47.27; H,7.90; N,11.11%. m/e 466 $(M+H)^+$.

EXAMPLE 23

N-[N-Methyl-N-(3-methyl-3-cyclohexenyl-(S)-α-aspartyl]-2(S)-[2-(N-amidino-4-piperidyloxy)ethyl]piperidine dihydrochloride Obtained from the title compound of Preparation 46 by analogy with Example 1. Rf 0.50 (SS 19). Found: C,48.01; H,7.82; N,11.00. $C_{25}H_{43}N_5O_4$; 2HCl; 1.10 H$_2$O; 0.90 CH$_2$Cl$_2$ requires C,48.09; H,7.64; N,10.83%. m/e 478.9 $(M+H)^+$.

EXAMPLE 24

N-(N-Cycloheptyl-N-methyl-(S)-α-aspartyl)-2(S)-[2-(N-amidino-4-piperidyloxy)ethyl]piperidine dihydrochloride Obtained from the title compound of Preparation 43 by analogy with Example 1. Rf 0.52 (SS 19). Found: C,49.77; H,8.12; N,11.47%. $C_{25}H_{45}N_5O_4$; 2HCl; 2H$_2$O; 0.25 CH$_2$Cl$_2$ requires C,49.73; H,8.51; N,11.48%. m/e 480.2 $(M+H)^+$.

EXAMPLE 25

N-[N-Methyl-N-(3,3-dimethylcyclohexyl)-(S)-α-aspartyl]-2(S)-[2-(N-amidino-4-piperidyloxy)ethyl]piperidine dihydrochloride Obtained from the title compound of Preparation 42 by analogy with Example 1. Rf 0.60 (SS 19). Found: C,50.18; H,8.49; N,10.84. $C_{25}H_{47}N_5O_4$; 2HCl; 2.50 H$_2$O; 0.20 CH$_2$Cl$_2$ requires C,50.06; H,8.72; N,11.14%. m/e 494 $(M+H)^+$.

EXAMPLE 26

N-(N-Cyclohexyl-N-methyl-(S)-α-aspartyl)-2(R,S)-[2-(N-amidino-4-piperidyloxy)ethyl]piperidine dihydrochloride Obtained from the title compound of Preparation 41 by analogy with Example 1. Rf 0.58 (SS 19). Found C,47.80; H,7.89; N,11.03. $C_{24}H_{43}N_5O_4$; 2HCl; 0.50 H$_2$O; CH$_2$Cl$_2$ requires C,47.47; H,7.65; N,11.07%. m/e 466 $(M+H)^+$.

EXAMPLE 27

N-(N-Cyclopentyl-N-methyl-(S)-α-aspartyl)-2(R,S)-[2-(N-amidino-4-piperidyloxy)ethyl]piperidine dihydrochloride Obtained from the title compound of Preparation 47 by analogy with Example 1. Rf 0.46 (SS 19). Found: C,48.06; H,7.76; N,1 1.67. $C_{23}H_{41}N_5O_4$; 2HCl; H$_2$O; 0.50 CH$_2$Cl$_2$ requires C,48.25; H,7.93; N,11.97%. m/e 452 $(M+H)^+$.

EXAMPLE 28

N-(N-Cycloheptyl-N-methyl-(S)-α-aspartyl)-2(R,S)-[2-(N-amidino-4-piperidyloxy)-ethyl]piperidine dihydrochloride Obtained from the title compound of Preparation 44 by analogy with Example 1. Rf 0.52 (SS 19). Found: C,46.93; H,7.88; N,10.64. $C_{25}H_{45}N_5O_4$; 2HCl; H$_2$O; CH$_2$Cl$_2$ requires C,47.21; H,7.77; N,10.55%. m/e 480 $(M+H)^+$.

EXAMPLE 29

N-(N-Cyclohexyl-N-ethyl-(S)-α-aspartyl)-2(R,S)-[2-(N-amidino-4-piperidyloxy)ethyl]piperidine dihydrochloride Obtained from the title compound of Preparation 48 by analogy with Example 1. Rf 0.54 (SS 19). Found: C,48.54; H,7.88; N,10.61. $C_{25}H_{45}N_5O_4$; 2HCl; 0.10 $H_2O$; $CH_2Cl_2$ requires C,48.85; H,7.76; N,10.95%. m/e 480.7 $(M+H)^+$.

EXAMPLE 30

N-[(2(S)-Carboxymethyl)piperidinoacetyl]-2(S)-[2-(N-amidino-4-piperidyloxy)ethyl]piperidine dihydrochloride Obtained from the title compound of Preparation 49 by analogy with Example 1. Rf 0.45 (SS 19). Found: C,44.68; H,7.62; N,1 1.32. $C_{22}H_{39}N_5O_4$; 2HCl; 1.50 $H_2O$; 0.90 $CH_2Cl_2$ requires C,44.80; H,7.52; N,11.41%.

EXAMPLE 31

N-(N-Cyclohexyl-(S)-α-aspartyl)-2(R,S)-[2-(4-amidinophenoxy)ethyl]piperidine dihydrochloride A 1M aqueous solution of sodium hydroxide (4.2 ml, 4.2 mmol) was added to a stirred suspension of the title compound of Preparation 59 (390 mg, 0.71 mmol) in 1,4-dioxan (4.2 ml). After a further 50 minutes, the resulting solution was acidified to pH3 with 1M hydrochloric acid and evaporated under reduced pressure; residual solvents were removed by azeotropy using 2-propanol. The resulting residue was extracted with hot 2-propanol, then the combined extracts filtered and evaporated under reduced pressure to afford the title compound (290 mg) as a white solid. Rf (diastereoisomers) 0.08 and 0.12 (SS 16). Found: C,54.81; H,7.97; N,9.61. $C_{24}H_{36}N_4O_4$; 2HCl; 0.70 $H_2O$; $CH_3CH(OH)CH_3$ requires C,54.95; H,8.09; N,9.49%. m/e 445 $(M+H)^+$.

EXAMPLE 32

N-[N-(N-Methyl-4-piperidyl)-(S)-α-aspartyl]-2(R, S)-[2-(4-amidinophenoxy)ethyl]-piperidine trihydrochloride Obtained from the title compound of Preparation 61 by analogy with Example 31. Rf 0.13 (SS 19). Found: C,48.57; H,7.52; N,10.74. $C_{24}H_{37}N_5O_4$; 3HCl; 1.90 $H_2O$; 0.40 $CH_3CH(OH)CH_3$ requires C,48.26; H,7.55; N,11.16%. m/e 443 $(M+H-NH_3)+$and 460 $(M+H)^+$.

EXAMPLE 33

N-[N-Methyl-N-(N-methyl-4-piperidyl)-(S)-α-aspartyl]-2(R,S)-[2-(4-amidinophenoxy)ethyl]piperidine trihydrochloride Obtained from the title compound of Preparation 66 by analogy with Example 31. Rf 0.13 (SS 19). Found: C,50.10; H,8.40; N,9.78. $C_{25}H_{39}N_5O_4$; 3 HCl; $2H_2O$; 1.20 $CH_3CH(OH)CH_3$; 0.30 $(C_2Hs)_2O$ requires C,50.17; H,8.27; N,9.81%. m/e 457 $(M+H-NH_3)+$and 474 $(M+H)^+$.

EXAMPLE 34

N-(N-4-Cycloheptenyl-(S)-α-aspartyl)-2(S)-[2-(N-amidinyloxy)-ethyl]piperidine dihydrochloride Obtained from the title compound of Preparation 67 by analogy with Example 1. Rf 0.60 (SS 19). Found: C,49.98; H,7.92; N,11.84. $C_{24}H_{41}N_5O_4$; 2HCl; 1.20 $H_2O$; 0.30 $CH_2Cl_2$ requires C,50.01; H,7.94; N,12.00%.

EXAMPLE 35

N-(N-4-Cycloheptenyl-N-methyl-(S)-α-aspartyl)-2(S)-[2-(N-amidino-4-piperidyloxy)ethyl]piperidine dichhydrochloride Obtained from the title compound of Preparation 68 by analogy with Example 1. Rf 0.54 (SS 19). Found: C,48.45; H,7.69; N,10.86. $C_{25}H_{43}N_5O_4$; 2HCl; 0.50 $H_2O$; $CH_2Cl_2$ requires C,48.45; H,7.51; N,10.87%. m/e 478 $(M+H)^+$.

EXAMPLE 36

N-(N-Cyclopropylmethyl-(S)-αaspartyl)-2(S)-[2-(N-amidine-4-piperidyloxy)ethyl]piperidine dihydrochloride Obtained from the title compound of Preparation 69 by analogy with Example 1. Rf 0.58 (SS 19). Found: C,45.14; H,7.84; N,12.19. $C_{21}H_{37}N_5O_4$; 2HCl; $2H_2O$; 0.40 $CH_2Cl_2$ requires C,45.37; H,7.79; N,12.36%. m/e 424 $(M+H)^+$.

EXAMPLE 37

N-(N-3-Pentyl-(S)-α-aspartyl)-2(S)-[2-(N-amidino-4-piperidyloxy)ethyl]piperidine dihydrochloride Obtained from the title compound of Preparation 70 by analogy with Example 1. Found: C,44.29; H,8.49; N,11.13. $C_{22}H_{41}N_5O_4$; 2HCl; $3H_2O$; 0.50 $CH_2Cl_2$ requires C,44.37; H,8.28; N,11.50%. m/e 440.6 $(M+H)^+$.

EXAMPLE 38

N-(N-2-Cyclohexyl-N-methyl-(S)-α-aspartyl)-2(S)-[2-(N-amidino-4-(piperidyloxy)ethyl]piperidine dihydrochloride Obtained from the title compound of Preparation 72 by analogy with Example 1. Rf 0.57 (SS 19). Found: C,48.91; H,8.15; N,11.90. $C_{24}H_{41}N_5O_4$; 2HCl; $3H_2O$ requires C,48.81; H,8.36; N,1 1.86%. m/e 464.3$(M+H)^+$.

EXAMPLE 39

N-(N-3(R)-Methylcyclohexyl-(S)-α-aspartyl)-2(S)-[2-(N-amidino-4-piperidyloxy)ethyl]piperidine dihydrochloride Obtained from the mixture of diastereoisomers of the title compound of Preparation 73 by analogy with Example 1. Rf 0.55 (SS 19). Found: C,48.97; H,8.18; N,11.54. $C_{24}H_{43}N_5O_4$; 2HCl; 1.50 $H_2O$ requires C,48.88; H,8.20; N,11.68%. m/e 466.5$(M+H)^+$.

EXAMPLE 40

N-(N-Methyl-N-3(R)-methylcyclohexyl-(S)-α-aspartyl)-2(S)-[2-(N-amidino-4-piperidyloxy)ethyl]piperidine dihydrochloride Obtained from the mixture of diastereoisomers of the title compound of Preparation 74 by analogy with Example 1. Rf 0.51 (SS 19). Found: C,50.26; H,8.59; N,1 1.69. $C_{25}H_{45}N_5O_4$; 2HCl; 2.60 $H_2O$ requires C,50.09; H,8.78; N, 11.68%. m/e 480.3 $(M+H)^+$.

A single diastereoisomer of the title compound was also obtained by effecting the corresponding deprotection of the single diastereoisomer from Preparation 74. Rf 0.57 (SS 19). m/e 480.2 $(M+H)^+$.

EXAMPLE 41

N-[N-Methyl-N-(2-norbornyl-(S)-α-aspartyl]-2(S)-[2-(N-amidino-4-piperidyloxy)ethyl]piperidine dihydrochloride Obtained from the title compound of Preparation 75 by analogy with Example 1. Rf 0.64 (SS 19). Found: C,50.39; H,8.09; N,11.52. $C_{25}H_{41}N_5O_4$; 2HCl; 2H$_2$O; 0.22 CH$_2$Cl$_2$ requires C,50.21; H,7.93; N,11.61%. m/e 492.2 (M+NH$_4$)$^+$.

EXAMPLE 42

N-[N-(3-Tetrahydropyranyl)-(S)-α-aspartyl]-2(S)-[2-(N-amidino-4-piperidyloxy)ethyl]piperidine dihydrochloride Obtained from the title compound of Preparation 77 by analogy with Example 1. Rf 0.53 (SS 19). Found: C,44.51; H,7.28; N,11.23. $C_{22}H_{39}N_5O_5$; 2HCl; 2H$_2$O; 0.50 CH$_2$Cl$_2$ requires C,44.67; H,7.66; N,11.58%. m/e 454.2 (M+H)$^+$.

EXAMPLE 43

N-[N-Methyl-N-(3-tetrahydropyranyl)-(S)-α-aspartyl]-2(S)-[2-(N-amidino-4-piperidyloxy)ethyl]piperidine dihydrochloride Obtained from the title compound of Preparation 78 by analogy with Example 1. Rf 0.52 (SS 19). Found: C,43.46; H,8.24; N,10.92. $C_{23}H_{41}N_5O_5$; 2HCl; 3.10 H$_2$O; 0.60 CH$_2$Cl$_2$ requires C,43.79; H,8.02; N,10.82%.

EXAMPLE 44

N-(N-3–Cyclohexenyl-(S)-a-aspartyl)-2(S)-[2-(N-amidino-4-piperidyloxy)ethyl]piperidine dihydrochloride Obtained from the title compound of Preparation 80 by analogy with Example 1. Rf 0.47 (SS 19). Found: C,47.32; H,7.76; N,11.28. $C_{23}H_{39}N_5O_4$; 2HCl; 2H$_2$O; 0.50 CH$_2$Cl$_2$ requires C,46.96; H,7.71; N,11.65%. m/e 450.0 (M+H)$^+$.

EXAMPLE 45

N-(N-3-Cyclohexenyl-N-methyl-(S)-α-aspartyl)-2(S)-[2-(N-amidino-4-piperidyloxy)ethyl]piperidine dihydrochloride Obtained from the title compound of Preparation 81 by analogy with Example 1. Rf 0.75 (SS 19). Found: C,46.46; H,8.20; N,10.85. $C_{24}H_{41}N_5O_4$; 2HCl; 3H$_2$O; 0.50 CH$_2$Cl$_2$ requires C,46.48; H,7.96; N,1 1.06%. m/e 464.3 (M+H)$^+$.

PREPARATION 1

2(S)-(2-Hydroxyethyl)piperidine

2(R,S)-(2-Hydroxyethyl)piperidine was resolved using (1S)-(+)-10-camphorsulphonic acid as described in Rec. Trav. chim., 1971, 90, 755 via the intermediate (S),(S)-10-camphorsulphonate salt, m.p. 167° C. (lit. 166–167° C.), $[\alpha]_D^{25}$+32.5° (c=2.2, CHCl$_3$) (reported in J. Amer. Chem. Soc., 1960, 82, 2613 as $[\alpha]_D$32.40 (c=2, CHCl$_3$)). The absolute configuration of the salt was determined by X-ray crystallographic analysis.

The title compound was obtained as fine needles, m.p. 69–70° C. (lit. 68–69° C.), Rf 0.25 (SS 1). GC analysis of the bis-trifluoroacetyl derivative, using a Chiraldex B-TA No C70 column, showed an enantiomeric excess (ee) of >98%.

PREPARATION 2

N-Benzyloxycarbonyl-2(S)-(2-hydroxyethyl)piperidine

To a stirred, ice-cooled solution of the title compound of Preparation 1 (13.4 g, 0.104 mol) in dichloromethane (250 ml) were added, sequentially, triethylamine (15.9 ml, 0.114 mol) and N-(benzyloxycarbonyloxy)succinimide (27.21 9, 0.109 mol). The cooling bath was removed, then the reaction mixture stirred at room temperature for 18 hours, washed with brine, dried (Na$_2$SO$_4$) and evaporated under reduced pressure to give an oil (30.6 g) which was purified by chromatography on silica gel, using hexane:ethyl acetate (1:1) as eluant, to provide the title compound (27.5 g) as an oil. Rf 0.48 (SS 2). $[\alpha]_D^{25}$–24.5° (c=1.06, CH$_3$OH).

PREPARATION 3

N-Benzyloxycarbonyl-2(R,S)-(2-hydroxyethyl)piperidine

Obtained from 2(R,S)-(2-hydroxyethyl)piperidine by analogy with Preparation 2. Rf 0.48 (SS 2). Found: C,68.27; H,8.26; N,5.28. $C_{15}H_{21}NO_3$ requires C,68.42; H,8.04; N,5.32%. m/e 264.4 (M+H)$^+$.

PREPARATION 4

N-Benzyloxycarbonyl-2(S)-(2-methanesulphonyloxyethyl)piperidine

Methanesulphonyl chloride (16.1 ml, 0.208 mol) was added dropwise over 15 minutes to a stirred, ice-cooled solution of the title compound of Preparation 2 (27.43 g, 0.104 mol) and triethylamine (29 ml, 0.208 mol) in dichloromethane (350 ml), the temperature of the reaction mixture being allowed to rise to 17° C. during the addition. After a further 25 minutes, the reaction mixture was washed with 1M aqueous citric acid solution, water and saturated aqueous sodium bicarbonate solution, dried (Na$_2$SO$_4$) and evaporated under reduced pressure to give a light yellow oil (40 g) which was purified by chromatography on silica gel, using hexane:ethyl acetate (1:1) as eluant, to furnish the title compound (33.5 g) as a clear oil which solidified on standing. Rf 0.59 (SS 8).

A trace of ethyl acetate was removed from the product azeotropically, using hexane, before the next step of the reaction sequence.

PREPARATION 5

N-Benzyloxycarbonyl-2(R,S)-(2-methanesulphonyloxyethyl)piperidine

Obtained from the title compound of Preparation 3 by analogy with Preparation 4. Rf 0.50 (SS 8). Found: C,54.76; H,6.35; N,4.10. $C_{16}H_{23}NO_5S$; 0.15 CH$_2$Cl$_2$ requires C,54.77; H,6.63; N,3.95%.

PREPARATION 6

N-t-Butoxycarbonyl-4-hydroxypiperidine

Di-t-butyl dicarbonate (35.58 g, 0.163 mol) was added to a stirred, ice-cooled solution of 4-hydroxypiperidine (15.0 g, 0.148 mol) in dichloromethane (250 ml). The cooling bath was removed, then the reaction mixture stirred at room temperature for 56 hours, washed with 1 M aqueous citric acid solution, dried (MgSO$_4$) and evaporated under reduced pressure to give a yellowish oil, treatment of which with hexane (20 ml), followed by chilling, promoted crystallisation. Filtration and washing of the product with cold hexane afforded the title compound (25.72 g). Rf 0.37 (SS 2). Found: C,59.27; H,9.70; N,6.96. $C_{10}H_{19}NO_3$ requires C, 59.68; H,9.51; N,6.96%.

PREPARATION 7

N-Benzyloxycarbonyl-2(S)-[2-(N -t-butoxycarbonyl-4-piperidyloxy)ethyl]piperidine The title compound of Preparation 6 (19.67 g, 97.5 mmol) was added to a stirred suspension of sodium hydride (60% dispersion in oil, 3.9 g, 97.5 mmol) in dry dimethylformamide (150 ml) under nitrogen. After 2 hours, a solution of the title compound of Preparation 4 (32.9 g, 96.4 mmol) in dry dimethylformamide (100 ml) was added and the resulting reaction mixture stirred for 18 hours. The bulk of the solvent was removed under reduced pressure, the residue diluted with water and the resulting oily suspension extracted with ethyl acetate (×3). The combined extracts were washed with brine, dried ($Na_2SO_4$) and evaporated under reduced pressure to give an oil which was purified by chromatography on silica gel, using hexane:ethyl acetate (7:3) as eluant, to afford the title compound (26.26 g) as an oil. Rf 0.35 (SS 3). $[\alpha]_D^{25}$–12.3° (c=1.01, $CH_3OH$). Found: C,67.07; H,8.75; N,6.04. $C_{25}H_{38}N_2O_5$ requires C,67.24; H,8.58; N,6.27%.

PREPARATION 8

N-Benzyloxycarbonyl-2(R,S)-[2-(N-t-butoxycarbonyl-4-piperidyloxy)ethyl]piperidine Obtained from the title compound of Preparation 5 by analogy with Preparation 7. Rf 0.30 (SS 3).

PREPARATION 9

N-Benzyloxycarbonyl-2(S)-[2-(4-piperidyloxy) ethyl]piperidine hydrochloride

A stirred, ice-cooled solution of the title compound of Preparation 7 (26.16 g, 58.6 mmol) in dichloromethane (300 ml) was saturated with hydrogen chloride. After a further 1.25 hours the solvent was removed by evaporation under reduced pressure and the residual hydrogen chloride removed azeotropically using dichioromethane to give the title compound (22.59 g) as a white foam. Rf 0.60 (SS 4). m/e 347.0 $(M+H)^+$.

PREPARATION 10

N-Benzyloxycarbonyl-2(R,S)-[2-(4-piperidyloxy) ethyl]piperidine hydrochloride

Obtained from the title compound of Preparation 8 by analogy with Preparation 9. Rf 0.50 (SS 5). Found: C,62.06; H,7.71; N,6.94. $C_{20}H_{30}N_2O_3$; HCl requires C,62.27; H,7.89; N,7.32%. m/e 347.0 $(M+H)^+$.

PREPARATION 11

N-Benzyloxycarbonyl-2(S)-{2-[N-(N,N'-di-t-butoxycarbonylamidino)-4-piperidyloxy] ethyl}piperidine Triethylamine (24.5 ml, 0.176 mol) was added to a stirred, ice-cooled solution of the title compound of Preparation 9 (22.59 g, 58.6 mmol) in dichloromethane (280 ml), the mixture allowed to warm to room temperature and then N,N'-di-t-butoxycarbonyl-S-methylisothiourea (J. Med. Chem., 1993, 36, 2956; 18.7 g, 64.4 mmol) and mercuric chloride (15.91 g, 58.6 mmol) added sequentially. The reaction mixture was stirred for 18 hours, for a further 2 hours under reflux, then filtered using an appropriate filter aid. The filtrate was washed with water, during which further filtration to remove precipitated material was necessary, dried ($Na_2SO_4$) and evaporated under reduced pressure to give crude product which was purified by chromatography on silica gel, using an elution gradient of hexane:ethyl acetate (7:3 to 1:1), to provide the title compound (30.37 g) as a gummy foam. Rf 0.20 (SS 2). $[\alpha]_D^{25}$–5.7° (c=1.1, $CH_3OH$). Found: C,62.42; H,8.30; N,9.31. $C_{31}H_{48}N_4O_7$ requires C,62.22; H,8.13; N,9.18%.

PREPARATION 12

N-Benzyloxycarbonyl-2(R,S)-{2-[N-(N,N'-di-t-butoxycarbonylamidino)-4-piperidyloxy] ethyl}piperidine Obtained from the title compound of Preparation 10 by analogy with Preparation 11. Rf 0.35 (SS 6). m/e 589.4 $(M+H)^+$.

PREPARATION 13

2(S)-{2-[N-(N,N'-di-t-butoxycarbonylamidino)-4-piperidyloxy]ethyl}piperidine

A solution of the title compound of Preparation 11 (26.82 g, 45.55 mmol) in absolute ethanol (400 ml) was hydrogenated over 10% palladium on charcoal (5.0 g) at room temperature and 414 kPa (60 psi) for 2.5 hours. The resulting mixture was filtered using a filter aid and the filtrate evaporated under reduced pressure to furnish the title compound (20.36 g) as a gum. Rf 0.13 (SS 7). $[\alpha]_D^{25}$–1.69° (c=1.3, $CH_3OH$). m/e 455 $(M+H)^+$.

PREPARATION 14

2(R,S)-{2-[N-(N,N'-di-t-butoxycarbonylamidino)-4-piperidyloxy]ethyl}piperidine

Obtained from the title compound of Preparation 12 by analogy with Preparation 13. Rf 0.22 (SS 7).

PREPARATION 15

N-[N-(9-Fluorenylmethoxycarbonyl)-O-t-butyl-(S)-α-aspartyl-2(S)-{2N-(N,N'-di-t-butoxycarbonylamidino)-4-piperidyloxy] ethyl}piperidine N-Ethyldiisopropylamine (1.27 ml, 4.6 mmol) was added to a stirred, ice-cooled solution of the title compound of Preparation 13 (1.05 g, 2.3 mmol), N-fluoroenylmethoxycarbonyl-(S)-aspartic acid β-t-butyl ester (946 mg, 2.3 mmol) and bromotris(pyrrolidino) phosphonium hexafluorophosphate (1.18 g, 2.5 mmol) in dry dichloromethane (6 ml). After 2.5 hours more coupling reagent (118 mg, 0.25 mmol) was added and stirring continued for a further 0.5 hour. The reaction mixture was diluted with ethyl acetate, washed sequentially with water, 1M aqueous citric acid, water, saturated aqueous sodium bicarbonate solution and brine, dried ($Na_2SO_4$) and evaporated under reduced pressure to give crude product (2.87 g) which was purified by chromatography on silica gel, using hexane:ethyl acetate (1:1) as eluant, to furnish the title compound (1.58 g) as a white foam. Rf 0.30 (SS 2). Found: C,64.42; H,8.05; N,8.24, $C_{46}H_{65}N_5O_{10}$; 0.40 $CH_3CO_2CH_2CH_3$ requires C,64.73; H,7.78; N,7.93%. m/e 626 (M−Fmoc+H)$^+$.

PREPARATION 16

N-[N-(9-Fluorenylmethoxycarbonyl)-O-t-butyl-(S)-α-aspartyl]-2(R,S)-{2-[N-(N,N'-di-t-butoxycarbonylamidino)-4-piperidyloxy]ethyl}piperidine Obtained from the title compound of Preparation 14 by analogy with Preparation 15. Rf 0.68 (SS 8). m/e 849 (M+H)$^+$.

PREPARATION 17

N-(O-t-Butyl-(S)-α-aspartyl)-2(S)-{2-[N-(N,N'-di-t-butoxycarbonylamidino)-4-piperidyloxy]ethyl}piperidine Piperidine (1.7 ml, 18.3 mmol) was added to a stirred solution of the title compound of Preparation 15 (1.55 g, 1.83 mmol) in tetrahydrofuran (7.5 ml). After 1 hour, the reaction mixture was evaporated under reduced pressure and the residue purified by chromatography on silica gel, using dichloromethane: methanol:0.880 aqueous ammonia (193:7:1) as eluant, to afford the title compound (1.05 g) as a white foam. Rf 0.50 (SS 7). Found: C,58.93; H,9.08; N,11.12. $C_{31}H_{55}N_5O_8$; 0.30 $H_2O$ requires C,58.99; H,8.88; N,11.09%. m/e 626 (M+H)$^+$.

PREPARATION 18

N-(O-t-Butyl-(S)-α-aspartyl)-2(R,S)-{2-[N-(N,N'-di-t-butoxycarbonylamidino)-4-piperidyloxy]ethyl}piperidine Obtained from the title compound of Preparation 16 by analogy with Preparation 17. Rf 0.52 (SS 8). m/e 626 (M+H)$^+$.

PREPARATION 19

N-[N-(N-Methyl-4-piperidyl)-O-t-butyl-(S)-α-aspartyl]-2(R,S)-{2-[N-(N,N'-di-t-butoxycarbonylamidino)-4-piperidyloxy]ethyl}piperidine To a stirred solution of the title compound of Preparation 18 (500 mg, 0.80 mmol) in anhydrous tetrahydrofuran (5 ml) was added N-methyl-4-piperidone (0.11 ml, 0.90 mmol) followed by glacial acetic acid (96 μl, 1.66 mmol). After a further 5 minutes sodium triacetoxyborohydride (254 mg, 1.12 mmol) was added and the reaction mixture stirred for 18 hours, then diluted with ethyl acetate (120 ml), washed with saturated aqueous sodium bicarbonate solution and brine, dried (MgSO$_4$) and evaporated under reduced pressure to give the crude product which was purified by chromatography on silica gel, using an elution gradient of dichloromethane:methanol:0.880 aqueous ammonia (100:0:0 to 100:5:0 to 200:15:1 to 200:15:2), to provide the title compound (0.51 g) as a white foam. Rf 0.50 (SS 9). Found: C,60.59; H,9.15; N,11.58. $C_{37}H_{66}N_6O_8$; 0.20 $CH_2Cl_2$ requires C,60.38; H,9.04; N,11.36%.

PREPARATION 20

N-[N-(3-Methyl-3-cyclohexenyl)-O-t-butyl-(S)-α-aspartyl]-2(S)-{2-[N-(N,N'-di-t-butoxycarbonylamidino)-4-piperidyloxy]ethyl}piperidine Obtained from the title compound of Preparation 17 and 3-methyl-3-cyclohexenone (J. Org. Chem., 1977, 42, 1051) by analogy with Preparation 19. Rf 0.96 (SS 10). Found: C,61.67; H,9.07; N,9.21. $C_{38}H_{65}N_5O_8$; 0.25 $CH_2Cl_2$ requires C,61.98; H,8.91; N,9.45%. m/e 720.3 (M+H)$^+$.

PREPARATION 21

N-Methyl-3-piperidone

A solution of anhydrous dimethyl sulphoxide (16.3 ml, 236 mmol) in dichloromethane (43 ml) was added, dropwise, to a stirred solution of oxalyl chloride (9.45 ml, 109 mmol) in dichloromethane at about −60° C. under nitrogen followed, 2 minutes later, by a solution of N-methyl-3-hydroxypiperidine (11.52 g, 100 mmol) in dichloromethane (100 ml). After a further 10 minutes, triethylamine (68.9 ml, 497 mmol) was also added dropwise and the reaction mixture stirred for a further 5 minutes at about −60° C. The cooling bath was then removed and the reaction mixture allowed to warm to room temperature before being treated with water (230 ml). The organic phase was separated, combined with dichloromethane extracts (2×250 ml) of the aqueous phase, washed with brine (500 ml), dried (MgSO$_4$) and evaporated under reduced pressure. The crude product was purified by distillation under reduced pressure to provide the title compound (6.8 g) as a clear oil, b.p. 58–64° C. at 1.33 kPa (10 mm Hg). m/e 114.1 (M+H)$^+$.

The somewhat unstable product was used immediately in the next step of the reaction sequence.

PREPARATION 22

N-[N-(N-Methyl-3-piperidyl)-O-t-butyl-(S)-α-aspartyl]-2(S)-{2-[N-(N,N'-di-t-butoxycarbonylamidino)-4-piperidyloxy]ethyl}piperidine Obtained from the title compounds of Preparation 17 and Preparation 21 by analogy with Preparation 19. Rf (diastereoisomers) 0.30 and 0.40 (SS 10). Found: C,59.32; H,9.01; N,11.06. $C_{37}H_{66}N_6O_8$; 0.40 $CH_2Cl_2$ requires C,59.35; H,8.90; N, 11.10%. m/e 723.9 (M+H)$^+$.

PREPARATION 23

N-[N-(2-Norbornyl)-O-t-butyl-(S)-α-aspartyl]-2(S)-{2-[N-(N,N'-di-t-butoxycarbonylamidino)-4-piperidyloxy]ethyl}piperidine Obtained from the title compound of Preparation 17 and (+)-2-norbornanone by analogy with Preparation 19. Rf 0.65 (SS 10). m/e 720.5 (M+H)$^+$.

PREPARATION 24

N-(N-Cyclohexyl-O-t-butyl-(S)-α-aspartyl)-2(S)-{2-[N-(N,N'-di-t-butoxycarbonylamidino)-4-piperidyloxy]ethyl}piperidine Obtained from the title compound of Preparation 17 and cyclohexanone by analogy with Preparation 19. Rf 0.80 (SS 7). m/e 708 (M+H)$^+$.

PREPARATION 25

N-(N-Cyclohexyl-O-t-butyl-(S)-α-aspartyl)-2(R,S)-{2-[N-(N,N'-di-t-butoxycarbonylamidino)-4-piperidyloxy]ethyl}piperidine Obtained from the title compound of Preparation 18 and cyclohexanone by analogy with Preparation 19. Rf 0.70 (SS 10). m/e 708.7 (M+H)$^+$.

27

PREPARATION 26

N-[N-(4-Tetrahydropyranyl)-O-t-butyl-(S)-α-aspartyl]-2(R,S)-{2-[N-(N,N'-di-t-butoxycarbonylamidino)-4-piperidyloxy]ethyl}piperidine Obtained from the title compound of Preparation 18 and 4-tetrahydropyranone by analogy with Preparation 19. Rf 0.60 (SS 10). m/e 710.5 (M+H)+.

PREPARATION 27

N-[N-(3,3-Dimethylcyclohexyl)-O-t-butyl-(S)-α-aspartyl]-2(S)-{2-[N-(N,N'-di-t-butoxycarbonylamidino)-4-piperidyloxy]ethyl}piperidine Obtained from the title compound of Preparation 17 and 3,3-dimethylcyclohexanone (J. Org. Chem., 1976, 41, 1069) by analogy with Preparation 19. Rf 0.62 (SS 10). m/e 736.3 (M+H)+.

PREPARATION 28

N-[N-(3,3-Dimethylcyclohexyl)-O-t-butyl-(S)-α-aspartyl]-2(R,S)-{2-[N-(N,N'-di-t-butoxycarbonylamidino)-4-piperidyloxy]ethyl}piperidine Obtained from the title compound of Preparation 18 and 3,3-dimethylcyclohexanone (J. Org. Chem., 1976, 41, 1069) by analogy with Preparation 19. Rf 0.62 (SS 10). m/e 736.9 (M+H)+.

PREPARATION 29

Cis-3,5-Dimethylcyclohexanone

A solution of 3,5-dimethyl-2-cyclohexenone (2.0 g, 16.1 mmol) in 2-propanol (32 ml) was hydrogenated over 5% palladium on charcoal (200 mg) at room temperature and 103 kPa (14.7 psi) for 4 hours, then diluted with 1:1 hexane:ether (150 ml) and filtered using a filter aid. The filtrate was evaporated under reduced pressure to provided the substantially stereochemically pure title compound (1.56 g) as a yellow oil. $^{13}$C NMR spectroscopy revealed a cis:trans ratio of 150:3.

PREPARATION 30

N-[N-(cis-3,5-Dimethylcyclohexyl)-O-t-butyl-(S)-α-aspartyl]-2(S)-{2-[N-(N,N'-di-t-butoxycarbonylamidino)-4-piperidyloxy]ethyl}piperidine Two diastereoisomers were obtained from the title compounds of Preparation 17 and Preparation 29 by analogy with Preparation 19 and separated by chromatography on silica gel, using an elution gradient of ethyl acetate:hexane (3:7 to 4:6), in a ca. 4:1 ratio.
Diasteroisomer A (major isomer)
  Rf 0.55 (SS 2). m/e 736.7 (M+H)+.
Diasteroisomer B (minor isomer)
  Rf 0.34 (SS 2). m/e 736.9 (M+H)+.

PREPARATION 31

N-(N-Cycloheptyl-O-t-butyl-(S)-α-aspartyl)-2(S)-{2-[N-(N,N'-di-t-butoxycarbonylamidino)-4-piperidyloxy]ethyl}piperidine Obtained from the title compound of Preparation 17 and cycloheptanone by analogy with Preparation 19. Rf 0.56 (SS 10). m/e 722.9 (M+H)+.

28

PREPARATION 32

N-(N-Cycloheptyl-O-t-butyl-(S)-α-aspartyl)-2(R,S)-{2-[N-(N,N'-di-t-butoxycarbonylamidino)-4-piperidyloxy]ethyl}piperidine Obtained from the title compound of Preparation 18 and cycloheptanone by analogy with Preparation 19. Rf 0.57 (SS 10). m/e 722.5 (M+H)+.

PREPARATION 33

N-(N-Cyclopentyl-O-t-butyl-(S)-α-aspartyl)-2(R,S)-{2-[N-(N,N'-di-t-butoxycarbonylamidino)-4-piperidyloxy]ethyl}piperidine Obtained from the title compound of Preparation 18 and cyclopentanone by analogy with Preparation 19. Rf 0.56 (SS 10). m/e 694.5 (M+H)+.

PREPARATION 34

N-(N-Cyclooctyl-O-t-butyl-(S)-α-aspartyl)-2(R,S)-{2-[N-(N,N'-di-t-butoxycarbonylamidino)-4-piperidyloxy]ethyl}piperidine Obtained from the title compound of Preparation 18 and cyclooctanone by analogy with Preparation 19. Rf 0.58 (SS 10). m/e 737 (M+H)+.

PREPARATION 35

N-[N-(2-Hydroxycyclohexyl)-O-t-butyl-(S)-α-aspartyl]-2(R,S)-{2-[N-(N,N'-di-t-butoxycarbonylamidino)-4-piperidyloxy]ethyl}piperidine A solution of the title compound of Preparation 18 in tetrahydrofuran (0.2 M; 20 μl), a solution of 2-hydroxycyclohexanone in tetrahydrofuran (0.2M; 22 μl), a suspension of sodium triacetoxyborohydride in tetrahydrofuran (0.2M; 30 μl) and a solution of glacial acetic acid in tetrahydrofuran (0.2M; 20 μl) were combined and the resulting mixture shaken at room temperature for 3 days, during which the solvent evaporated. The crude product was purified by chromatography on silica gel, using dichloromethane:methanol (95:5) as eluant, to give the title compound. Rf 0.26 (SS 11). m/e 724.4 (M+H)+.

PREPARATION 36

N-[N-(3-Tetrahydrothiopyranyl)-O-t-butyl-(S)-α-aspartyl]-2(R,S)-{2-[N-(N,N'-di-t-butoxycarbonylamidino)-4-piperidyloxy]ethyl}piperidine Obtained from the title compound of Preparation 18 and 3-tetrahydrothiopyranone by analogy with Preparation 35, but using an elution gradient of dichloromethane:methanol (100:0 to 95:5) for chromatographic purification. Rf 0.38 (SS 1 1). m/e 726.4 (M+H)+.

PREPARATION 37

N-[N-(4-Tetrahydrothiopyranyl)-O-t-butyl-(S)-α-aspartyl]-2(R,S)-{2-[N-(N,N'-di-t-butoxycarbonylamidino)-4-piperidyloxy]ethyl}piperidine A solution of the title compound of Preparation 18 in 1,2-dichloroethane (0.2M; 25 μl), a solution of 4-tetrahydrothiopyranone in 1,2-dichloroethane (0.2 M; 50 μl), a suspension of sodium triacetoxyborohydride in 1,2-dichloroethane (0.2 M; 50 μl) and 5 beads of pre-activated (ca. 120° C. in vacuo) 4Å molecular sieves were combined and the resulting mixture shaken at room temperature for 3 days, during which the solvent evaporated. The crude product was purified by chromatography on silica gel, using an elution gradient of dichloromethane:methanol (100:0 to 95:5), to provide the title compound. Rf 0.79 (SS 10). m/e 726.3 (M+H)$^+$.

PREPARATION 38

N-(N-Cyclohexylmethyl)-O-t-butyl-(S)-α-aspartyl)-2(R,S)-{2-[N-(N,N'-di-t-butoxycarbonylamidino)-4-piperidyloxy]ethyl}piperidine Sodium triacetoxyborohydride (185 mg, 0.88 mmol) was added in one portion to a stirred mixture of the title compound of Preparation 18 (276 mg, 0.44 mmol) and cyclohexanecarboxaldehyde (0.107 ml, 0.88 mmol) in dry tetrahydrofuran (5 ml) under nitrogen at room temperature, then the resulting mixture stirred for 3.5 hours and evaporated under reduced pressure. The residue was partitioned between ethyl acetate and saturated aqueous sodium bicarbonate solution, then the organic phase separated, washed with brine, dried (MgSO$_4$) and evaporated under reduced pressure to give a foam which was purified by chromatography on silica gel, using hexane:ethyl acetate (1:1) as eluant, to furnish the title compound (137 mg) as a crystallised foam. Rf 0.80 (SS 2). m/e 723 (M+H)$^+$.

PREPARATION 39

N-( N-Cyclopentylmethyl-O-t-butyl-(S)-α-aspartyl)-2(S)-{2-[N-(N,N'-di-t-butoxycarbonylamidino)-4-piperidyloxy]ethyl}piperidine Obtained from the title compound of Preparation 17 and cyclopentanecarboxaldehyde (Org. Syn. Coll. Vol. 5, 1973, 320) by analogy with Preparation 38, but using 1.5 mol. equivs. of sodium triacetoxyborohydride. Rf 0.27 (SS 2). $[\alpha]_D^{25}$ –0.7° (c=0.7, CH$_3$OH). m/e 708 (M+H)$^+$.

PREPARATION 40

N-(N-Cyclohexyl-N-methyl-O-t-butyl-(S)-α-aspartyl)-2(S)-{2-[N-(N,N'-di-t-butoxycarbonylamidino)-4-piperidyloxy]ethyl}piperidine Aqueous formaldehyde solution (37%; 0.34 ml, 4.15 mmol) was added to a stirred solution of the title compound of Preparation 24 (735 mg, 1.04 mmol) in dichloromethane (15 ml) followed, 1 hour later, by sodium triacetoxyborohydride (440 mg, 2.08 mmol). After a further 1 hour, the reaction mixture was diluted with dichloromethane, washed sequentially with saturated aqueous sodium bicarbonate solution and brine, dried (Na$_2$SO$_4$) and evaporated under reduced pressure to give a gum (810 mg) which was purified by chromatography on silica gel, using an elution gradient of dichloromethane:methanol:0.880 aqueous ammonia (393:7:1 to 293:7:1), to afford the title compound (720 mg) as a white foam. Rf 0.32 (SS 12). Found: C,62.53; H,9.34; N,9.31. C$_{38}$H$_{67}$N$_5$O; 0.50 H$_2$O requires C,62.44; H,9.37; N,9.58%. m/e 722 (M+H)$^+$.

PREPARATION 41

N-(N-Cyclohexyl-N-methyl-O-t-butyl-(S)-α-aspartyl)-2(R,S)-{2-[N-(N,N'-di-t-butoxycarbonylamidino)-4-piperidyloxy]ethyl}piperidine Obtained from the title compound of Preparation 25 by analogy with Preparation 40. Rf 0.75 (SS 10). m/e 722.6 (M+H)$^+$.

PREPARATION 42

N-[N-Methyl-N-(3,3-dimethylcyclohexyl)-O-t-butyl-(S)-α-astartyl]-2(S)-{2-[N-(N,N'-di-t-butoxycarbonylamidino)-4-piperidyloxy]ethyl}piperidine Obtained from the title compound of Preparation 27 by analogy with Preparation 40. Rf 0.78 (SS 10). m/e 751 (M+H)$^+$.

PREPARATION 43

N-(N-Cycloheptyl-N-methyl-O-t-butyl-(S)-α-aspartyl)-2(S)-{2-[N-(N,N'-di-t-butoxycarbonylamidino)-4-piperidyloxy]ethyl}piperidine Obtained from the title compound of Preparation 31 by analogy with Preparation 40. Rf 0.74 (SS 10). m/e 736.6 (M+H)$^+$.

PREPARATION 44

N-(N-Cycloheptyl-N-methyl-O-t-butyl-(S)-α-aspartyl)-2(R,S)-{2-[N-(N,N'-di-t-butoxycarbonylamidino)-4-piperidyloxy]ethyl}piperidine Obtained from the title compound of Preparation 32 by analogy with Preparation 40. Rf 0.74 (SS 10). m/e 736.7 (M+H)$^+$.

PREPARATION 45

N-[N-Methyl-N-(cis-3,5-dimethylcyclohexyl)-O-t-butyl-(S)-α-aspartyl]-2(S)-{2-[N-(N,N'-di-t-butoxycarbonylamidino)-4-piperidyloxy]ethyl}piperidine Obtained from diastereoisomer A of the title compound of Preparation 30 by analogy with Preparation 40. Rf 0.73 (SS 2). Found: C,63.49; H,9.45; N,9.24. C$_{40}$H$_{71}$N$_5$O$_8$; 0.50 H$_2$O requires C,63.30; H,9.56; N,9.23. m/e 750.7 (M+H)$^+$.

PREPARATION 46

N-[N-Methyl-N-(3-methyl-3-cyclohexenyl)-O-t-butyl-(S)-α-aspartyl]-2(S)-{2-[N-(N,N'-di-t-butoxycarbonylamidino)-4-piperidyloxy]ethyl}piperidine Obtained from the title compound of Preparation 20 by analogy with Preparation 40. Rf 0.75 (SS 2). m/e 734.5 (M+H)$^+$.

PREPARATION 47

N-(N-Cyclopentyl-N-methyl-O-t-butyl-(S)-α-aspartyl)-2(R,S)-{2-[N-(N,N'-di-t-butoxycarbonylamidino)-4-piperidyloxy]ethyl}piperidine Obtained from the title compound of Preparation 33 by analogy with Preparation 40. Rf 0.76 (SS 10). m/e 708.5 (M+H)$^+$.

PREPARATION 48

N-(N-Cyclohexyl-N-ethyl-O-t-butyl-(S)-α-aspartyl)-2(R,S)-{2-[N-(N,N'-di-t-butoxycarbonylamidino)-4-piperidyloxy]ethyl}piperidine A solution of acetaldehyde in tetrahydrofuran (1M; 0.97 ml, 0.97 mmol) was added to a stirred solution of the title compound of Preparation 25 (328 mg, 0.463 mmol) followed, 0.5 hour later, by sodium triacetoxyborohydride (216 mg, 1.02 mmol). After 18 hours, further portions of the acetaldehyde solution (1M; 0.34 ml, 0.34 mmol) and sodium triacetoxyborohydride (72 mg, 0.34 mmol) were added, then the reaction mixture stirred for 3 hours more and evaporated under reduced pressure. The residual solid was partitioned between ethyl acetate and water, then the organic phase separated, washed sequentially with saturated aqueous sodium bicarbonate solution and brine, dried ($MgSO_4$) and evaporated under reduced pressure. The crude product was purified by chromatography on silica gel, using hexane:ethyl acetate (1:1) as eluant, to provide the title compound (193 mg) as a white foam. Rf 0.87 (SS 13). Found: C,62.42; H,9.36; N,9.13. $C_{39}H_{69}N_5O_8$; 0.20 $CH_2Cl_2$ requires C,62.53; H,9.29; N,9.30%. m/e 736.3 $(M+H)^+$.

PREPARATION 49

N-[(2(S)-t-Butoxycarbonylmethyl)piperidinoacetyl]-2(S)-{2-[N-(N,N'-di-t-butoxycarbonylamidino)-4-piperidyloxy]ethyl}piperidine An aqueous solution of glutaraldehyde (50 wt. %; 0.1 ml, 0.50 mmol) was added to a stirred solution of the title compound of Preparation 17 (212 mg, 0.338 mmol) in dichloromethane (5 ml) followed, 0.5 hour later, by sodium triacetoxyborohydride (109 mg, 0.51 mmol). After a further 1.75 hours, the reaction mixture was diluted with dichloromethane (30 ml), then washed sequentially with saturated aqueous sodium bicarbonate solution and brine, dried ($MgSO_4$) and evaporated under reduced pressure to give an oil which was purified by chromatography on silica gel, using hexane:ethyl acetate (6:4) as eluant, to afford the title compound (137 mg) as a glass-like solid. Rf 0.53 (SS 2). $[\alpha]_D^{25}$ –11.70 (c=0.3, $CH_3OH$). m/e 694 $(M+H)^+$.

PREPARATION 50

N-[N-(9-Fluorenylmethoxycarbonyl)-O-t-butyl-(S)-α-glutamyl]-2(R,S)-{2-[N-(N,N'-di-t-butoxycarbonylamidino)-4-piperidyloxy]ethyl}piperidine A suspension of 1-ethyl-3-(3-dimethylamino-1-propyl) carbodiimide hydrochloride (348 mg, 2.00 mmol) in dichloromethane (7 ml) was added in one portion to a stirred, ice-cooled mixture of the title compound of Preparation 14 (470 mg, 1.03 mmol), N-fluorenylmethoxycarbonyl-(S)-glutamic acid-γ-t-butyl ester (426 mg, 1.00 mmol), 1-hydroxybenzotriazole monohydrate (137 mg, 1.01 mmol), N-methylmorpholine (220 µl, 2.00 mmol) and dichloromethane (17 ml) under nitrogen. After 20 minutes the cooling bath was removed and the reaction mixture stirred for a further 17 hours and then evaporated under reduced pressure. The residue was partitioned between ethyl acetate and water, then the organic phase separated, washed with saturated aqueous sodium bicarbonate solution and brine, dried ($MgSO_4$) and evaporated under reduced pressure to give an oil which was purified by column chromatography on silica gel, using an elution gradient of hexane:ethyl acetate (6:4 to 4:6), to afford the title compound (244 mg) as a foam. Rf 0.32 (SS 2). Found: C,65.40; H,7.93; N,7.66. $C_{47}H_{67}N_5O_{10}$ requires C,65.48; H,7.83; N,8.12%. m/e 640 $(M-Fmoc+H)^+$.

PREPARATION 51

N-(O-t-Butyl-(S)-α-glutamyl)-2(R,S)-{2-[N-(N,N'-di-t-butoxycarbonylamidino)-4-piperidyloxy]ethyl}piperidine Obtained from the title compound of Preparation 50 by analogy with Preparation 17. Rf 0.26 (SS 8). m/e 640 $(M+H)^+$.

PREPARATION 52

N-(N-Cyclohexyl-O-t-butyl-(S)-α-glutamyl)-2(R,S)-{2-[N-(N,N'-di-t-butoxycarbonylamidino)-4-piperidyloxy]ethyl}piperidine Obtained from the title compound of Preparation 51 and cyclohexanone by analogy with Preparation 19. Rf 0.55 (SS 13). m/e 722 $(M+H)^+$.

PREPARATION 53

N-t-Butoxycarbonyl-2(R,S)-(2-hydroxyethyl) piperidine

A solution of di-t-butyl dicarbonate (10.91 g, 50 mmol) in ethyl acetate (15 ml) was added to a stirred, ice-cooled solution of 2(R,S)-(2-hydroxyethyl)piperidine (5.06 g, 50 mmol) in ethyl acetate (25 ml), then the cooling bath was removed. After a further 1.5 hours the reaction mixture was evaporated under reduced pressure and the residue purified by chromatography on silica gel, using hexane:ether (1:1) as eluant, to provide the title compound (8.46 g, 74%) as a clear oil. Rf 0.25 (SS 14).

PREPARATION 54

N-t-Butoxycarbonyl-2(R,S)-[2-(4-cyanophenoxy) ethyl]piperidine

Diethyl azodicaboxylate (1.73 ml, 11 mmol) was added to a stirred, ice-cooled solution of the title compound of Preparation 53 (2.29g, 10 mmol) and 4-cyanophenol (1.31 g, 11 mmol) in tetrahydrofuran (75 ml), then the cooling bath was removed. After a further 18 hours the reaction mixture was evaporated under reduced pressure and the residue dissolved in ether. The resulting solution was washed with 1M aqueous sodium hydroxide solution and brine, dried ($Na_2SO_4$) and evaporated under reduced pressure to give crude product which was purified by chromatography on silica gel, using hexane:ether (1:1) as eluant, to furnish the title compound (2.86 g) as a clear oil which solidified on standing. Rf 0.30 (SS 14). Found: C,69.20; H,8.32; N,8.42. $C_{19}H_{26}N_2O_3$ requires C,69.06; H,7.93; N,8.49%.

PREPARATION 55

2(R,S)-[2-(4-Cyanophenoxy)ethyl]piperidine

Trifluoroacetic acid (10 ml) was added to a stirred, ice-cooled solution of the title compound of Preparation 54 (2.83 g, 8.56 mmol) and anisole (1.88 ml, 17.3 mmol) in dry dichloromethane (15 ml). After a further 1 hour the reaction mixture was evaporated under reduced pressure, the residue dissolved in water and the solution washed with ether, basified with 2M aqueous sodium hydroxide solution and thrice extracted with ether. The combined extracts were washed with brine, dried ($Na_2SO_4$) and evaporated under reduced pressure to afford the title compound (1.43 g) as an oil which solidified on standing. Rf 0.15 (SS 7). m/e 231 $(M+H)^+$.

PREPARATION 56

N-(N-t-Butoxycarbonyl-O-benzyl-(S)-α-aspartyl)-2(R,S)-[2-(4-cyanophenoxyethyl]piperidine Obtained as a white foam from the title compound of Preparation 55 and N-t-butoxycarbonyl-(S)-aspartic acid β-benzyl ester (1.2 mol. equiv.) by analogy with Preparation 15, using hexane:ether (1:3) as the eluant for chromatographic purification. Rf (diastereoisomers) 0.30 and 0.41 (SS 15). Found: C,66.88; H,6.75; N,7.80. $C_{30}H_{37}N_3O_6$ requires C,67.27; H,6.96; N,7.84%. m/e 536 $(M+H)^+$.

PREPARATION 57

N-(O-Benzyl-(S)-α-aspartyl)-2(R,S)-{2-(4-cyanophenoxy)ethyl}piperidine

Trifluoroacetic acid (8 ml) was added to a stirred, ice-cooled solution of the title compound of Preparation 56 (3.0 g, 5.6 mmol) and anistle (1.2 ml, 11.2 mmol) in dry dichloromethane (15 ml). After a further 2 hours the reaction mixture was evaporated under reduced pressure, the residue dissolved in ether and the solution extracted with water. After five extractions a heavy oil separated and this was removed with the aqueous phase; a further twenty aqueous extractions were required to obtain all the desired product. The combined aqueous extracts (ca. 600 ml), together with the insoluble oil, were basified to pH 11 with 10M aqueous sodium hydroxide solution and then extracted with dichloromethane. The organic extract was washed with brine, dried ($Na_2SO_4$) and evaporated under reduced pressure to provide the title compound (2.25 g) as a viscous oil. Rf (diastereoisomers) 0.28 and 0.38 (SS 7). m/e 436 $(M+H)^+$.

PREPARATION 58

N-(N-Cyclohexyl-O-benzyl-(S)-α-aspartyl)-2(R,S)-[2-(4-cyanophenoxy)ethyl]piperidine Sodium triacetoxyborohydride (585 mg, 2.76 mmol) was added to a stirred solution of the title compound of Preparation 57 (802 mg, 1.84 mmol), cyclohexanone (0.23 ml, 2.2 mmol) and glacial acetic acid (0.12 ml, 2 mmol) in tetrahydrofuran (10 ml). After a further 1.7 hours the reaction mixture was evaporated under reduced pressure, the residue partitioned between ethyl acetate and saturated aqueous sodium bicarbonate solution, and the organic solution separated, washed with brine, dried ($Na_2SO_4$) and evaporated under reduced pressure to give a gum (970 mg) which was purified by chromatography on silica gel, using hexane:ethyl acetate (1:1) as eluant, to furnish the title compound (840 mg) as a gum. Rf 0.25 (SS 2). Found: C,70.77; H,7.36; N,7.78. $C_{31}H_{39}N_3O_4$; 0.50 $H_2O$ requires C,70.70; H,7.65; N,7.98%. m/e 518 $(M+H)^+$.

PREPARATION 59

N-(N-Cyclohexyl-O-ethyl/benzyl (9/1)-(S)-α-aspartyl)-2(R,S)-[2-(4-amidinophenoxy)ethyl]piperidine dihydrochloride A stirred, ice-cooled solution of the title comopund of Preparation 58 (810 mg, 1.56 mmol) in absolute ethanol (10 ml) which had been dried over 3Å molecular sieves was saturated with hydrogen chloride and then left at about 0° C. for 3 days. The reaction mixture was evaporated under reduced pressure, residual hydrogen chloride removed azeotropically with ethanol and the residue dried in vacuo to give the intermediate imino ether hydrochloride as a white foam. Rf 0.50 (SS 7).

A solution of this intermediate in ethanolic ammonia (1.96M; 5.2 ml, 10.17 mmol) was heated at 50° C. for 3 hours and then evaporated under reduced pressure. The residue was dissolved in water, then the solution washed with ether, basified with 1M aqueous sodium hydroxide solution and extracted with dichloromethane. The organic extract was washed with brine, dried ($Na_2SO_4$), treated with excess ethereal hydrogen chloride and evaporated under reduced pressure to afford the title compound (790 mg) as a white powder. Rf 0.30 (SS 16). Found: C,56.17; H,7.56; N,9.68. $C_{26}H_{40}N_4O_4$; 2HCl; 0.125 $CH_2Cl_2$ requires C,56.45; H,7.66; N,10.08%. m/e 473 $(M+H)^+$-ethyl ester.

The ratio of ethyl to benzyl ester (ca. 9:1) was indicated by $^1H$ NMR spectroscopy.

PREPARATION 60

N-[N-(N-Methyl-4-piperidyl)-O-benzyl-(S)-α-aspartyl]-2(R,S)-[2-(4-cyanophenoxy)ethyl]piperidine Obtained as a gum from the title compound of Preparation 57 and N-methyl-4-piperidone by analogy with Preparation 58. Rf (diastereoisomers) 0.28 and 0.33 (SS 7). m/e 533 $(M+H)^+$.

PREPARATION 61

N-[N-(N-Methyl-4-piperidyl)-O-ethyl/benzyl(2/3)-(S)-aspartyl]-2(R,S)-[2-(4-amidinophenoxy)ethyl]piperidine trihydrochloride Obtained as a white powder from the title compound of Preparation 60 by analogy with Preparation 59. Rf (diastereoisomers) 0.17 and 0.24 (SS 16). m/e 488 $(M+H)^+$-ethyl ester, 550 $(M+H)^+$-benzyl ester.

PREPARATION 62

N-t-Butoxycarbonyl-4-piperidone

A solution of di-t-butyl dicarbonate (56.8 g, 0.26 mole) in acetonitrile (100 ml) was added dropwise to a stirred, ice-cooled suspension of 4-piperidone hydrochloride monohydrate (40.0 g, 0.26 mole) in triethylamine (26.3 g, 0.26 mole) and acetonitrile (300 ml). After a further 5 days the reaction mixture was filtered and the filtrate evaporated under reduced pressure to give an off-white solid (69 g) which was purified by chromatography on silica gel, using hexane:ether (1:1) as eluant, to provide the title compound (37.5 g) as a white solid, m.p. 74–75° C. Rf 0.60 (SS 17). Found: C,60.36; H,8.78; N,6.88. $C_{10}H_{17}NO_3$ requires C,60.28; H,8.60; N,7.03%.

PREPARATION 63

N-[N-(N-t-Butoxycarbonyl-4-piperidyl)-O-benzyl-(S)-α-aspartyl]-2(R,S)-[2-(4-cyanophenoxy)ethyl]piperidine Obtained as a gum from the title compounds of Preparation 57 and Preparation 62 by analogy with Preparation 58. Rf (diastereoisomers) 0.33 and 0.43 (SS 18). Found: C,67.71; H,7.96; N,8.64. $C_{35}H_{46}N_4O_6$ requires C,67.94; H,7.49; N,9.05%. m/e 619 $(M+H)^+$, 519 $(M-Boc+2H)^+$.

PREPARATION 64

N-[N-(4-Piperidyl)-O-benzyl-(S)-α-aspartyl]-2(R,S)-[2-(4-cyanophenoxy)ethyl]piperidine Obtained as a foam from the title compound of Preparation 63 by analogy with Preparation 55. Rf (diastereoisomers) 0.12 and 0.16 (SS 7). m/e 519 $(M+H)^+$.

PREPARATION 65

N-[N-Methyl-N-(N-methyl-4-piperidyl)-O-benzyl-(S)-α-aspartyl]-2(R,S)-[2-(4-cyanophenoxy)ethyl]piperidine Obtained as a gum from the title compound of Preparation 64 by analogy with Preparation 40, but using 5 mol. equiv.

of formaldehyde. Rf 0.60 (SS 7). Found: C,70.23; H,8.17; N,9.84. $C_{32}H_{42}N_4O_4$ requires C,70.30; H,7.74; N,10.25%. m/e 547 $(M+H)^+$.

PREPARATION 66

N-[N-Methyl-N-(N-methyl-4-piperidyl)-O-ethyl/benzyl(1/4)-(S)-α-aspartyl]-2(R,S)-[2-(4-amidinophenoxy)ethyl]piperidine trihydrochloride Obtained as a white powder from the title compound of Preparation 65 by analogy with Preparation 59. Rf (diastereoisomers) 0.26 and 0.32 (SS 16). m/e 502 $(M+H)^+$-ethyl ester, 564 $(M+H)^+$-benzyl ester.

PREPARATION 67

N-(N-4-Cycloheptenyl-O-t-butyl-(S)-α-aspartyl)-2(S)-{2-[N-(N,N'-di-t-butoxycarbonylamidino)-4-piperidyloxy]ethyl}piperidine Obtained from the title compound of Preparation 17 and 4-cycloheptenone. (J. Org Chem., 1982, 42, 693) by analogy with Preparation 19. Rf 0.39 (SS 2); 0.76 (SS 10). Found: C,63.04; H,9.12; N,9.65. $C_{35}H_{65}N_5O_8$ requires C,63.39; H,9.10; N,9.73%. m/e 720 $(M+H)^+$.

PREPARATION 68

N-(N-4-Cycloheptenyl-N-methyl-O-t-butyl-(S)-α-aspartyl)-2(S)-{2-[N-(N,N'-di-t-butoxycarbonylamidino)-4-piperidyloxy]ethyl}piperidine Obtained from the title compound of Preparation 67 by analogy with Preparation 40. Rf 0.63 (SS 2); 0.66 (SS 8). Found: C,63.11; H,9.24; N,9.38. $C_{39}H_{67}N_5O_8$; 0.50 $H_2O$ requires C,63.05; H,9.22; N,9.43%. m/e 734 $(M+H)^+$.

PREPARATION 69

N-(N-Cyclopropylmethyl-O-t-butyl-(S)-α-aspartyl)-2(S)-{2-[N-(N,N'-di-t-butoxycarbonylamidino)-4-piperidyloxy]ethyl}piperidine Obtained from the title compound of Preparation 17 and cyclopropanecarboxaldehyde by analogy with Preparation 38. Rf 0.10 (SS 2). $[\alpha]_D^{25}$ –2.6° (c=0.6, $CH_3OH$). m/e 681 $(M+H)^+$.

PREPARATION 70

N-(N-3-Pentyl-O-t-butyl-(S)-α-aspartyl)-2(S)-{2-[N-(N,N'-di-t-butoxycarbonylamidino)-4-piperidyloxy]ethyl}piperidine Obtained from the title compound of Preparation 17 and 3-pentanone by analogy with Preparation 19. m/e 696.2 $(M+H)^+$.

PREPARATION 71

N-(N-2-Cyclohexenyl-O-t-butyl-(S)-α-aspartyl)-2(S)-{2-[N-(N,N'-di-t-butoxycarbonylamidino)-4-piperidyloxy]ethyl}piperidine Potassium carbonate (190 mg, 1.37 mmol) was added to a stirred solution of the title compound of Preparation 17 (300 mg, 0.48 mmol) in acetonitrile (3 ml), followed by a solution of 3-bromocyclohexene (80 mg, 0.50 mmol) in acetonitrile (1 ml), and the mixture heated under reflux for 24 hours. A further portion of 3-bromocyclohexene (80 mg, 0.50 mmol) was then added to the cool reaction mixture and stirring under reflux continued for a further 24 hours. The resulting reaction mixture was evaporated under reduced pressure and the residue partitioned between ethyl acetate (150 ml) and water (150 ml). The organic phase was separated, washed with brine (150 ml), dried ($MgSO_4$) and evaporated under reduced pressure to give a white foam which was purified by chromatography on silica gel, using hexane:ethyl acetate (2:1) as eluant, to provide the title compound (300 mg) as a white foam. Rf 0.43 (SS 2). Found: C,64.49; H,10.03; N,9.60. $C_{37}H_{63}N_5O_8$; 0.67 $C_6H_{14}$ requires C,64.50; H,9.56; N,9.14%. m/e 706.3 $(M+H)^+$.

PREPARATION 72

N-(N-2-Cyclohexenyl-N-methyl-O-t-butyl-(S)-α-aspartyl)-2(S)-{2-[N-(N,N'-di-t-butoxycarbonylamidino)-4-piperidyloxy]ethyl}piperidine Obtained from the title compound of Preparation 71 by analogy with Preparation 40. Rf 0.31 (SS 2). Found: C,63.33; H,9.17; N,9.26. $C_{38}H_{65}N_5O_8$; 0.07 $CH_2Cl_2$ requires C,62.99; H,9.05; N,9.65%. m/e 720.3 $(M+H)^+$.

PREPARATION 73

N-(N-3(R)-Methylcyclohexyl-O-t-butyl-(S)-α-aspartyl)-2(S)-{2-[N-(N,N'-di-t-butoxycarbonylamidino)-4-piperidyloxy]ethyl}piperidine Obtained as a mixture of diastereoisomers from the title compound of Preparation 17 and 3(R)-methylcyclohexanone by analogy with Preparation 19. Rf 0.47 and 0.58 (SS 2). Found: C,63.06; H,9.37; N,9.47. $C_{38}H_{67}N_5O_8$ requires C,63.21; H,9.35; N,9.70%. m/e 722.7 $(M+H)^+$.

Repeated chromatography on silica gel, using hexane-:ethyl acetate (3:1) as eluant, allowed isolation of the major, higher-running (Rf 0.58, SS 2) diastereoisomer. m/e 722.7 $(M+H)^+$.

PREPARATION 74

N-(N-Methyl-N-3(R)-methylcyclohexyl-O-t-butyl-(S)-α-aspartyl)-2(S)-{2-[N-(N,N'-di-t-butoxycarbonylamidino)-4-piperidyloxy]ethyl}piperidine Obtained as a mixture of diastereoisomers from the title compound of Preparation 73 (mixture of diastereoisomers) by analogy with Preparation 40. Rf 0.90 (SS 19).

A single diastereoisomer of the title compound was also obtained by effecting the corresponding N-methylation of the major, higher-running diastereoisomer from Preparation 73. Rf 0.57 (SS 2). Found: C,64.20; H,9.81; N,9.22. $C_{39}H_{69}N_5O_8$ requires C,63.64; H,9.45; N,9.52%.

PREPARATION 75

N-[N-Methyl-N-(2-norbornyl)-d-t-butyl-(S)-α-aspartyl]-2(S)-{2-[N-(N,N'-di-t-butoxycarbonylamidino)-4-piperidyloxy]ethyl}piperidine Obtained from the title compound of Preparation 23 by analogy with Preparation 40. Rf 0.70 (SS 2). Found:

C,63.23; H,9.18; N,9.41. $C_{39}H_{67}N_5O_8$; 0.05 $CH_2Cl_2$ requires C,63.53; H,9.16; N,9.49%.

PREPARATION 76

3-Tetrahydropyranone

Obtained as a yellow oil from 3-hydroxytetrahydropyran (J. Org. Chem., 1970, 35, 898) by a procedure similar to that described for Preparation 21.

PREPARATION 77

N-[N-(3-Tetrahydropyranyl)-O-t-butyl-(S)-α-aspartyl]-2(S)-{2-[N-(N,N'-di-t-butoxycarbonylamidino)-4-piperidyloxy]ethyl}piperidine Obtained from the title compounds of Preparation 17 and Preparation 76 by analogy with Preparation 19. Rf 0.79 (SS 8). Found: C,59.89; H,8.84; N,9.46. $C_{36}H_{63}N_5O_9$; 0.20 $CH_2Cl_2$ requires C,59.81; H,8.79; N,9.65%.

PREPARATION 78

N-[N-Methyl-N-(3-tetrahydropyranyl)-O-t-butyl-(S)-α-aspartyl]-2(S)-{2-[N-(N,N'-di-t-butoxycarbonylamidino)-4-piperidyloxy]ethyl}piperidine Obtained from the title compound of Preparation 77 by analogy with Preparation 40. Rf 0.83 (SS 10). Found: C,60.14; H,9.01; N,9.21. $C_{37}H_{65}N_5O_9$; 0.20 $CH_2Cl_2$ requires C,60.30; H,8.90; N,9.45%. m/e 723.8 (M+H)$^+$.

PREPARATION 79

3-Cyclohexenone

Obtained from anisole by analogy with the method described in J. Org. Chem., 1977, 42, 1051 for the preparation of 3-methyl-3-cyclohexenone (see Preparation 20) from 3-methylanisole. B.p. 66–69° C. 1.33 kPa (10 mm Hg). ν c=o 1725 cm$^{-1}$. Found: C,73.45; H,8.54. $C_6H_8O$; 0.03 $CH_2Cl_2$ requires C,73.40; H,8.23%.

PREPARATION 80

N-(N-3-Cyclohexenyl-O-t-butyl-(S)-α-aspartyl)-2(S)-{2-[N-(N,N'-di-t-butoxycarbonylamidino)-4-piperidyloxy]ethyl}piperidine Obtained from the title compounds of Preparation 17 and Preparation 79 by analogy with Preparation 19. Rf 0.92 (SS 10). Found: C,61.56; H,8.79; N,9.18. $C_{37}H_{63}N_5O_8$; 0.30 $CH_2Cl_2$ requires C,61.25; H,8.76; N,9.57%. m/e 706.7 (M+H)$^+$.

PREPARATION 81

N-(N-3–Cyclohexenyl-N-methyl-O-t-butyl-(S)-α-aspartyl)-2(s)-{2-[N-(N,N'-di-t-butoxycarbonylamidino)-4-piperidyloxy]ethyl}piperidine Obtained from the title compound of Preparation 80 by analogy with Preparation 40. Rf 0.84 (SS 8). Found: C,62.80; H,9.15; N,9.31. $C_{38}H_{65}N_5O_8$; 0.10 $CH_2Cl_2$ requires C,62.82; H,9.02; N,9.61%. m/e 720.6 (M+H)$^+$.

Biological activity

The following Table illustrates the in vitro inhibitory activities against thrombin and trypsin for a range of the compounds of the invention.

TABLE

| EXAMPLE | Ki(M) | |
|---|---|---|
| | THROMBIN | TRYPSIN |
| 3 | $4.1 \times 10^{-9}$ | $1.2 \times 10^{-6}$ |
| 16 | $1.3 \times 10^{-9}$ | $7.2 \times 10^{-7}$ |
| 17 | $3.5 \times 10^{-8}$ | $1.1 \times 10^{-5}$ |
| 25 | $2.0 \times 10^{-9}$ | $3.6 \times 10^{-7}$ |
| 29 | $1.6 \times 10^{-8}$ | $5.0 \times 10^{-6}$ |
| 31 | $4.5 \times 10^{-8}$ | $1.3 \times 10^{-6}$ |

Safety profile

Certain compounds of the invention have been tested at 1 mg/kg i.v. in rat without showing any sign of adverse toxicity. One of these compounds has also been tested at 10 mg/kg i.v. in rat and at doses of up to 10 mg/kg i.v. in mouse; again no sign of adverse toxicity was apparent.

We claim:

1. A compound of formula (I):

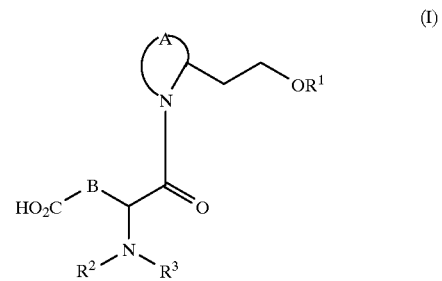

(I)

or a pharmaceutically acceptable salt thereof, or a pharmaceutically acceptable solvate of either entity, wherein A is optionally monounsaturated $C_4$–$C_5$ alkylene optionally substituted with $C_1$–$C_4$ alkyl;

B is $C_1$–$C_3$ alkylene optionally substituted with $C_1$–$C_4$ alkyl;

$R^1$ is N-amidino-4-piperidyl or 4-amidinophenyl;

$R^2$ is $C_4$–$C_{12}$ alkyl; ($C_3$–$C_8$ cycloalkyl)$C_1$–$C_4$ alkylene; optionally methylene-bridged $C_5$–$C_8$ cycloalkyl optionally substituted with one to three $C_1$–$C_4$ alkyl groups or with hydroxy; $C_5$–$C_8$ alkenyl;

$C_5$–$C_8$ cycloalkenyl optionally substituted with $C_1$–$C_4$ alkyl; piperidyl N-substituted with $C_1$–$C_4$ alkyl; tetrahydrothiopyranyl or tetrahydropyranyl;

and $R^3$ is H or $C_1$–$C_4$ alkyl optionally substituted with $C_1$–$C_4$ alkoxy or with hydroxy;

or $R^2$ and $R^3$, together with the nitrogen atom to which they are attached, form a piperidine ring which is optionally substituted with $C_1$–$C_4$ alkyl or is optionally benzo-fused.

2. A compound according to claim 1 wherein the preferred stereoisomer is of formula (IA):

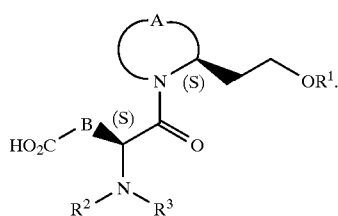

(IA)

3. A compound according to claim 2 wherein A is butylene; B is $C_1$–$C_2$ alkylene; $R^2$ is $C_4$–$C_6$ alkyl; ($C_3$–$C_6$ cycloalkyl)$CH_2$; $C_5$–$C_8$ cycloalkyl optionally substituted with one to three methyl groups or with hydroxy; norbornyl; $C_6$–$C_7$ cycloalkenyl optionally substituted with methyl; piperidyl N-substituted with methyl; tetrahydrothiopyranyl or tetrahydropyranyl; $R^3$ is H, methyl or ethyl; or $R^2$ and $R^3$, together with the nitrogen atom to which they are attached, form a piperidine ring substituted with methyl.

4. A compound according to claim 3 wherein A is butylene; B is methylene; $R^1$ is N-amidino-4-piperidyl; $R^2$ is 3-pentyl; ($C_5$–$C_6$ cycloalkyl)$CH_2$; cyclopentyl; cyclohexyl optionally substituted with one or two methyl groups; 2-hydroxycyclohexyl; 2-norbornyl; cycloheptyl; cyclooctyl; cyclohexenyl optionally substituted with methyl; cycloheptenyl; 3-tetrahydrothiopyranyl; 4-tetrahydropyranyl or 3-tetrahydropyranyl; and $R^3$ is H, methyl or ethyl.

5. A compound according to claim 4 wherein A is butylene; B is methylene; $R^1$ is N-amidino-4-piperidyl; $R^2$ is cyclohexyl; 3-methylcyclohexyl; 3,3-dimethylcyclohexyl; 3,5-dimethylcyclohexyl; 2-norbornyl; cycloheptyl; cyclooctyl; 3-cyclohexenyl; 3-methyl-3-cyclohexenyl or 4-cycloheptenyl; and $R^3$ is H or methyl.

6. A compound according to claim 5 which is selected from

N-(N-cycloheptyl-N-methyl-(S)-α-aspartyl)-2(S)-[2-(N-amidino-4-piperidyloxy)ethyl]piperidine;

N-(N-4-cycloheptenyl-N-methyl-(S)-α-aspartyl)-2(S)-[2-(N-amidino-4-piperidyloxy)ethyl]piperidine;

N-(N-methyl-N-3(R)-methylcyclohexyl-(S)-α-aspartyl)-2(S)-[2-(N-amidino-4-piperidyloxy)ethyl]piperidine; and N-(N-cyclohexyl-N-methyl-(S)-α-aspartyl)-2(S)-[2-(N-amidino-4-piperidyloxy)ethyl]piperidine;

and pharmaceutically acceptable salts thereof, and pharmaceutically acceptable solvates of either entity.

7. A pharmaceutical composition comprising a compound of claim 1, or a pharmaceutically acceptable salt thereof, or a pharmaceutically acceptable solvate of either entity, together with a pharmaceutically acceptable diluent or carrier.

8. A compound of formula (II):

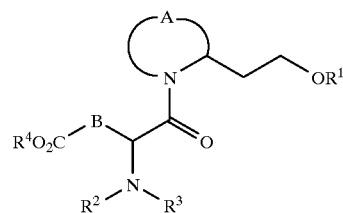

(II)

wherein $R^4$ is $C_1$–$C_4$ alkyl or benzyl, A, B, $R^2$ and $R^3$ are as previously defined in claim 1, and the amidino group in $R^1$ as defined in claim 1 is optionally protected.

9. A method of treating a mammal to cure or prevent deep vein thrombosis (DVT) after surgery, major medical illness, paralysis, malignancy, prolonged immobilization trauma, application of lower limb plaster casts, or fractures of the lower limbs or pelvis; recurrent DVT; DVT during pregnancy when there is a previous history thereof; reocculsion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extra-corporeal circuits; occulsion of arterio-venous shunts and blood vessel grafts (including coronary artery by-pass grafts); restonosis and occlusion following angioplasty; neurodegenerative disorders; inflammatory disorders; or scarring; which comprises treating said mammal with an effective amount of compound of claim 1, or a pharmaceutically acceptable salt thereof, or a pharmaceutically acceptable solvate of either entity.

* * * * *